US008809558B1

(12) United States Patent
Williams et al.

(10) Patent No.: US 8,809,558 B1
(45) Date of Patent: Aug. 19, 2014

(54) SYNTHETIC METHODS AND INTERMEDIATES FOR THE PREPARATION OF XENICANES

(75) Inventors: Lawrence J. Williams, New Brunswick, NJ (US); Michael Drahl, New Brunsiwck, NJ (US); Madhuri Manpadi, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 13 days.

(21) Appl. No.: 13/215,931

(22) Filed: Aug. 23, 2011

Related U.S. Application Data

(60) Provisional application No. 61/376,200, filed on Aug. 23, 2010, provisional application No. 61/448,015, filed on Mar. 1, 2011.

(51) Int. Cl.
*C07D 303/32* (2006.01)
(52) U.S. Cl.
CPC .................................. *C07D 303/32* (2013.01)
USPC .......................................................... 549/546
(58) Field of Classification Search
CPC ..................................................... C07D 303/32
USPC .......................................... 549/546; 568/339
See application file for complete search history.

(56) References Cited

U.S. PATENT DOCUMENTS

2010/0113585 A1    5/2010  Falkowski

OTHER PUBLICATIONS

Larionov et al., J. Ame. Chem. Soc. (2008) vol. 130(10), pp. 2954-2966.*
Zhang et al., Tetrahed. Letts. (2009), vol. 50(17), pp. 1882-1885.*
Karrer, Org. Chem. 2nd Ed., (1946) Elsevier Publ. Comp., Inc. NY, pp. 92-102.*
Aebi et al., "Sesquiterpenoids. Part III. The Stereochemistry of Caryophyllene", *J. Chem. Soc.*, 3124-3129 (1953).
Aebi et al., "Sesquiterpenoids. Part V. The Stereochemistry of theTricyclic Derivatives of Caryophyllene", *J. Chem. Soc.*, 4659-4665 (1954).
Altmann et al.,"Total synthesis of the marine diterpenoid blumiolide C", *Angew. Chem., Int. Ed.*, 47, 10081-10085 (2008).
Andrianasolo et al., "Induction of Apoptosis by Diterpenes from the Soft Coral *Xenia elongate*", *J. Nat. Prod.*, 70 (10), 1551-1557 (2007).
Anta et al., "New Xenia diterpenoids from the Indonesian soft coral Xenia sp.", *J. Nat. Prod.*, 65 (5), 766-768 (2002).
Bada et al., "Racemization Reaction of Aspartic Acid and its Use in Dating Fossil Bones", *Proc. Nat. Acad. Sci.*, 70 (5), 1331-1334, (1973).
Bertz et al., "Effect of TMSCI on theConjugate Addition of Organocuprates to a-Enones: A New Mechanism", *J. Am. Chem. Soc.*, 117, 11023-11024 (1995).
Chapdelaine et al., "A Convergent Synthesis of the Cardenolide Skeleton: Intramolecular Aldol Condensation via Reduction of α-Bromoketones", *J. Org. Chem.*, 67 (16), 5669-5672 (2002).
Chen et al., "Biomimetic Syntheses of the Neurotrophic Natural Products Caryolanemagnolol and Clovanemagnolol", *Org. Lett.*, vol. 12 (6), 1304-1307 (2010).
Cope et al., "Molecular Asymmetry of Olefins. III. Optical Stability of trans-Cyclononene and trans-Cyclodecene", *J. Am. Chem. Soc.*, 87, 3644-3649 (1965).
Corey et al., "An Unconventional Approach to the Enantioselective Synthesis of Caryophylloids", *J. Am. Chem. Soc.*, 130 (10), 2954-2955 (2008).
Degenhardt et al., "A Mouse Model System to Genetically Dissect the Molecular Mechanisms Regulating Tumorigenesis", *Clin. Cancer Res.*, 12 (18), 5298-5304 (2006).
Duh et al., "New cytotoxic xenia diterpenoids from the Formosan soft coral Xenia umbellate", *J. Nat. Prod.*, 65 (12), 1882-1885 (2002).
El-Gamal et al., "Xenibellols A and B, new diterpenoids from the formosan soft coral Xenia umbellate", *Org. Lett.*, vol. 7 (10), 2023-2025 (2005).
El-Gamal et al., "Cytotoxic xenia diterpenoids from the soft coral Xenia umbellate", *J. Nat. Prod.*, 69 (3), 338-341 (2006).
Fattorusso et al., "Xenimanadins A-D, a Family of Xenicane Diterpenoids from the Indonesian Soft Coral Xenia sp.", *Tetrahedron*, 64, 3141-3146 (2008).
Faulkner, "Marine Natural Products: Metabolites of Marine Algae and Herbivorous Marine Molluscs", *Nat. Prod. Rep.*, 1, 251-280 (1984).
Fenical, *Marine Natural Products*, P.J. Scheuer Ed. Academic Press, New York, 2, 173-245 (1978).
Finer et al., "Structures of Dictyodial and Dictyolactone, Unusual Marine Diterpenoids", *J. Org. Chem.*, 44, 2044-2047 (1979).
Gansäuer et al., "A Radical Tandem Reaction with Homolytic Cleavage of a Ti-O-Bond", *Angew. Chem. Int. Ed.*, 42, 3687-3690, (2003).
Gansäuer et al., "A Radical Roundabout for an Unprecedented Tandem Reaction Including a Homolytic Substitution with a Titanium-Oxygen Bond", *Eur. J. Org. Chem.*, 2337-2351, (2004).
Groweiss et al., "Xeniculin, Xeniaphyllenol and Xeniaphyllenol Oxide, New Diterpenoids from the Soft-Coral Xenia Macrospiculata", *Tetrahedron Lett.*, 25, 2205-2208 (1978).
Groweiss et al., "Xeniolide-A and Xeniolide-B, Two New Diterpenoids from the Soft-Coral Xenia Macrospiculata", *Tetrahedron Lett.*, 48, 4833-4836 (1978).
Groweiss et al., "Eight New Xenia Diterpenoids from Three Soft Corals of the Red Sea", *Tetrahedron*, 39 (20), 3385-3396 (1983).
Guella et al., "Joalin, the First Nitrogen-containing Xenicane Diterpene Isolated from a Brown Seaweed Collected off the Senegalese Coast", *J. Chem. Soc. Perkin Trans. 1*, 1545-1546 (1993).
Guella et al., "109. Xenicane Diterpenes Revisited: Thermal (E) → (Z) Isomerization and Conformational Motions. A Unifying Picture", *Helv. Chim. Acta.*, 77, 1203-1221 (1994).
Hiroaki et al., "Two New Xenicane Diterpenoids from Okinawan Soft Coral of the Genus, Xenia", *Heterocycles*, 61, 189-196 (2003).
Hooper et al., "New Diterpenes from the South African Soft Coral Eleutherobia aurea", *J. Nat. Prod.*, 60, 889-893 (1997).

(Continued)

*Primary Examiner* — Taofiq A Solola
(74) *Attorney, Agent, or Firm* — Viksnins Harris & Padys PLLP

(57) ABSTRACT

The invention provides novel synthetic intermediates and synthetic methods that are useful for preparing compounds of the xenicane family. Certain compounds of the invention may also possess anti-cancer properties.

3 Claims, 1 Drawing Sheet

(56) References Cited

OTHER PUBLICATIONS

Huddleston et al., "Enolate Generation under Hydrogenation Conditions: Catalytic Aldol Cycloreduction of Keto-Enones", *Org. Lett.*, 5 (7), 1143-1146 (2003).

Iwagawa et al., "Phosphine-mediated [2 +2] Cycloaddition of Internal Alk-2-ynoate and Alk-2-ynone to [60]Fullerene", *J. Chem. Soc. Chem. Commun.*, 2473-2474 (1995).

Iwagawa et al., "New Xenia Diterpenoids from a Soft Coral, Xenia Species", *Tetrahedron*, 51 (41), 11111-11118 (1995).

Iwagawa et al., "New DI- and Tricarbocyclic Diterpenes Possessing a Bicyclic [4.3.1] Ring System Isolated from the Soft Coral, Xenia Florida", Treahedron, 53 (20), 6809-6816 (1997).

Iwagawa et al., "New xenia diterpenes isolated from the soft coral, xenia florida", *J. Nat. Prod.*, 61 (12), 1513-1515 (1998).

Iwagawa et al., "New Xenicane Diterpenes Isolated from the Acetone Extract of the Soft Coral Xenia florida", *J. Nat. Prod.*, 63, 468-472 (2000).

Kashman et al., "Xeniafaraunol A and B, and Faraunatin; Three New Cytotoxic Diterpenes from the Soft Coral Xenia Faraunensis", *Tetrahedron Lett.*, 35 (47), 8855-8858 (1994).

Kim et al., "Concise synthesis of the xenibellols core", *Tetrahedron Lett.*, 50, 6440-6441 (2009).

Leumann et al., "Total Synthesis of Coraxeniolide-A", *J. Org. Chem.*, 65, 9069-9079 (2000).

Lin et al., "Asterolaurins A—F, Xenicane Diterpenoids from the Taiwanese Soft Coral Asterospicularia laurae", *J. Nat. Prod.*, 72 (11), 1911-1916 (2009).

Miyamoto et al., "Bioactive diterpenoids from Octocorallia, 2. Deoxyxeniolide B, a novel ichthyotoxic diterpenoid from the soft coral Xenia elongate", *J. Nat. Prod.*, 58 (6), 924-928 (1995).

Miyaoka et al., "Three New Xenicane Diterpenoids from Okinawan Soft Coral of the Genus, Xenia", *Tetrahedron*, 55, 12977-12982 (1999).

Miyaoka et al., "Xeniaoxolane: A New Xenicane-type Diterpenoid from the Okinawan Soft Coral, Xenia sp.; Absolute Configurations of Xeniaoxolane, Xeniolide-A and Xenialactol", *Tetrahedron*, 56, 7737-7740 (2000).

Mushti et al., "Total Synthesis of Antheliolide A", *J. Am. Chem. Soc.*, 128 (43), 14050-14052 (2006).

Nugent et al., "Transition-metal-centered radicals in organic synthesis. Titanium(III)-induced cyclization of epoxy olefins", *J. Am. Chem. Soc.*, 110 (25), 8561-8562 (1988).

Rajanbabu et al., "Selective Generation of Free Radicals from Epoxides Using a Transition-Metal Radical. A Powerful New Tool for Organic Synthesis", *J. Am. Chem. Soc.*, 116, 986-997 (1994).

Schlunzen et al., "Structural basis for the interaction of antibiotics with the peptidyl transferase centre in eubacteria", *Nature*, 413, 814-821 (2001).

Shen et al., "New xenicane diterpenoids from Xenia florida", *Tetrahedron Lett.*, 46 (28), 4793-4796 (2005).

Vanderah et al., "Marine Natural Products. Xenicin: a Diterpenoid Possessing a Nine-Membered Ring from the Soft Coral, Xenia elongate", *J. Am. Chem. Soc.*, 99, 5780-5784 (1977).

Williams et al., "Studies for the Synthesis of Xenicane Diterpenes. A Stereocontrolled Total Synthesis of 4-Hydroxydictyolactone", *J. Am. Chem. Soc.*, 131 (25), 9038-9045 (2009).

* cited by examiner

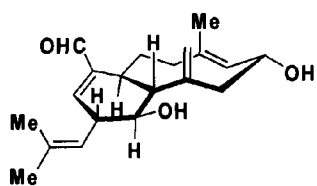

xeniafaraunol A
MIC$_{50}$ = 1.2 ug/mL vs. P388,
Tet. Lett. 1994, 35, 8855.

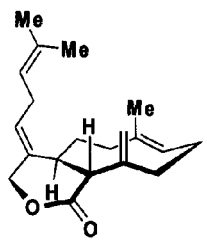

deoxyxeniolide B
LC$_{50}$ = 15 ppm vs. *Orizias latipa*,
J. Nat. Prod. 1995, 58, 924.

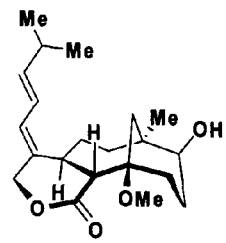

florlide B
100 ug/disk vs.
*Staphylococcus aureus*,
*Aeromonas salmonisida*,
J. Nat. Prod. 1998, 61, 1513.

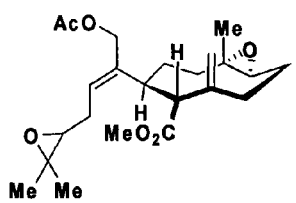

xenitacin
MIC$_{50}$ = 1.09 ug/mL vs. P388,
3.26 ug/mL vs. A-549,
1.12 ug/mL vs. HT-29,
J. Nat. Prod. 2002, 65, 1882.

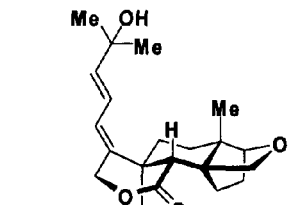

xenibellol A (xeniolactone A)
MIC$_{50}$ = 2.8 ug/mL vs. P388,
13.6 ug/mL vs. WiDr,
15.3 ug/mL vs. Daoy,
Org. Lett. 2005, 7, 2023.
Tet. Lett. 2005, 46, 4793.

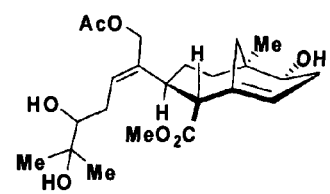

umbellacin E
MIC$_{50}$ = 3.8 ug/mL vs. P388,
J. Nat. Prod. 2006, 69, 338.

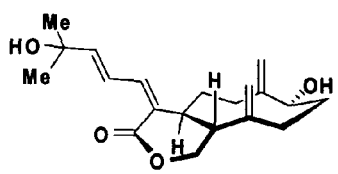

xeniolide F
> 1 ug/mL vs. P388, A-549,
HT-29, MEL-28,
J. Nat. Prod. 2002, 65, 766.

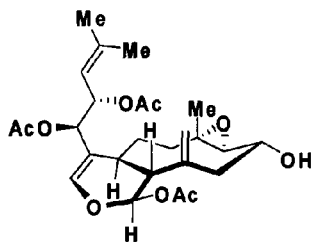

asterolaurin A
MIC$_{50}$ = 8.9 uM vs. HepG2,
J. Nat. Prod. 2009, 72, 1911.

SYNTHETIC METHODS AND INTERMEDIATES FOR THE PREPARATION OF XENICANES

STATEMENT OF GOVERNMENT RIGHTS

The invention was made with the support of a grant from the National Science Foundation (Grant No: CHE-1012379). The Government has certain rights in the invention.

PRIORITY OF INVENTION

This application claims priority from U.S. Provisional Application No. 61/376,200, filed 23 Aug. 2010, and from U.S. Provisional Application No. 61/448,015, filed 1 Mar. 2011. The entire content of each of these provisional applications is hereby incorporated by reference herein.

BACKGROUND OF THE INVENTION

Xenicanes are a family of diterpene natural products. As shown in FIG. 1, representative members of the xenicane family have been reported to possess a variety of beneficial biological properties (also see for Example *J. Nat. Prod.* 2007, 70, 1551).

Compounds of the xenicane family vary in oxidation state of the cores and side chains. Some derivatives possess additional rings. The florlides contain a methylene bridge across the nine-membered ring, while the xenibellols possess a tricyclic core including a tetrahydrofuran ring. The absolute configuration and features of relative stereochemistry of many of these compounds are unknown; however, the absolute configuration for some isolates has been shown to vary depending upon the producing organism (e.g. soft corals/sea fans vs. symbiotic brown algae). There are at least twelve classes in the greater xenicane family consisting of over one hundred natural products; however, only four total syntheses (excluding xeniaphyllanes) have been reported to date. See Leumann et al., *J. Org. Chem.*, 2000, 65, 9069; Corey et al., *J. Am. Chem. Soc.* 2008, 130, 2954; Altmann et al. *Angew. Chem. Int. Ed.* 2008, 47, 10081; and Williams et al., *J. Am. Chem. Soc.* 2009, 131, 9038.

Even though the xenicanes and related compounds, broadly defined, have been known in the literature for over thirty years, their scarcity and structural complexity have prevented the structure-activity relationship (SAR) studies necessary to enable complete medicinal valuation. Accordingly, there is currently a need for synthetic intermediates and methods that can be used to prepare xenicane compounds.

SUMMARY OF THE INVENTION

A new nine-membered ring scaffold containing an α,β-unsaturated carboxylate functionality that is useful for preparing xenicanes has been developed. The new molecular platform is obtainable in racemic form in ten chemical steps. Accordingly, in one embodiment the invention provides a A compound of formula 1:

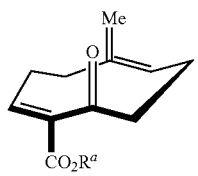

wherein:

$R^a$ is H, $(C_1\text{-}C_6)$alkyl, $(C_2\text{-}C_6)$alkenyl, $(C_2\text{-}C_6)$alkynyl, $(C_3\text{-}C_8)$cycloalkyl, $(C_3\text{-}C_8)$cycloalkyl$(C_1\text{-}C_6)$alkyl, aryl, or heteroaryl, wherein each $(C_1\text{-}C_6)$alkyl, $(C_2\text{-}C_6)$alkenyl, $(C_2\text{-}C_6)$alkynyl, $(C_3\text{-}C_8)$cycloalkyl, and $(C_3\text{-}C_8)$cycloalkyl$(C_1\text{-}C_6)$alkyl of $R^a$ is optionally substituted with one or more groups independently selected from halo, hydroxy, cyano, nitro, $(C_1\text{-}C_6)$alkoxy, $(C_3\text{-}C_8)$cycloalkyl, oxo, carboxy, aryl, aryloxy, and —$NR^bR^c$; and wherein each aryl, and heteroaryl of $R^a$ is optionally substituted with one or more groups independently selected from $(C_1\text{-}C_6)$alkyl, halo, hydroxy, cyano, carboxy, nitro, trifluoromethyl, trifluoromethoxy, $(C_1\text{-}C_6)$alkoxy, $(C_1\text{-}C_6)$alkoxycarbonyl, $(C_1\text{-}C_6)$alkanoyloxy, and —$NR^bR^c$; and $R^b$ and $R^c$ are each independently selected from H, $(C_1\text{-}C_6)$alkyl, $(C_3\text{-}C_8)$cycloalkyl, $(C_3\text{-}C_8)$cycloalkyl$(C_1\text{-}C_6)$alkyl, aryl, heteroaryl, aryl$(C_1\text{-}C_6)$ alkyl and heteroaryl$(C_1\text{-}C_6)$alkyl; or $R^b$ and $R^c$ together with the nitrogen to which they are attached form a aziridino, azetidino, morpholino, piperazino, pyrrolidino or piperidino.

In another embodiment the invention provides a method for preparing an ester of formula 1:

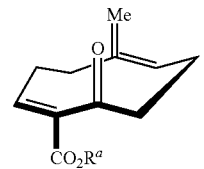

wherein $R^a$ is H, $(C_1\text{-}C_6)$alkyl, $(C_2\text{-}C_6)$alkenyl, $(C_2\text{-}C_6)$alkynyl, $(C_3\text{-}C_8)$cycloalkyl, $(C_3\text{-}C_8)$cycloalkyl$(C_1\text{-}C_6)$alkyl, aryl, or heteroaryl, wherein each $(C_1\text{-}C_6)$alkyl, $(C_2\text{-}C_6)$alkenyl, $(C_2\text{-}C_6)$alkynyl, $(C_3\text{-}C_8)$cycloalkyl, and $(C_3\text{-}C_8)$cycloalkyl $(C_1\text{-}C_6)$alkyl of $R^a$ is optionally substituted with one or more groups independently selected from halo, hydroxy, cyano, nitro, $(C_1\text{-}C_6)$alkoxy, $(C_3\text{-}C_8)$cycloalkyl, oxo, carboxy, aryl, aryloxy, and —$NR^bR^c$; and wherein each aryl, and heteroaryl of $R^a$ is optionally substituted with one or more groups independently selected from $(C_1\text{-}C_6)$alkyl, halo, hydroxy, cyano, carboxy, nitro, trifluoromethyl, trifluoromethoxy, $(C_1\text{-}C_6)$alkoxy, $(C_1\text{-}C_6)$alkoxycarbonyl, $(C_1\text{-}C_6)$alkanoyloxy, and —$NR^bR^c$; and $R^b$ and $R^c$ are each independently selected from H, $(C_1\text{-}C_6)$alkyl, $(C_3\text{-}C_8)$cycloalkyl, $(C_3\text{-}C_8)$cycloalkyl$(C_1\text{-}C_6)$alkyl, aryl, heteroaryl, aryl$(C_1\text{-}C_6)$ alkyl and heteroaryl$(C_1\text{-}C_6)$alkyl; or $R^b$ and $R^c$ together with the nitrogen to which they are attached form a aziridino, azetidino, morpholino, piperazino, pyrrolidino or piperidino;

comprising converting an acid of formula 2:

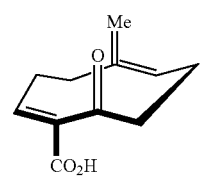

to the ester of formula 1.

In another embodiment the invention provides a compound of formula 1, 2, 3, 4, 4a, 4b, 4c, 4d, 5, 6, 10, 11b, 12, 13, 14, 20, 23, 24, 25, 26, 27, 30, or 31:
1
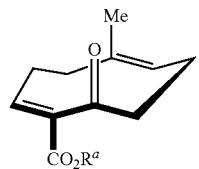
2
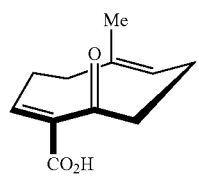
3
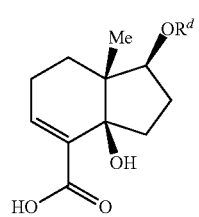
4
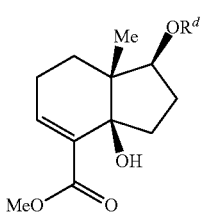
4a
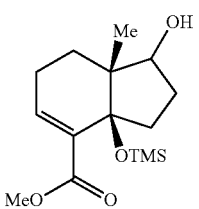
4b
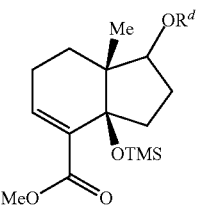
4c
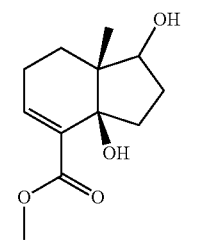
-continued
4d
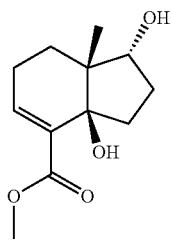
5
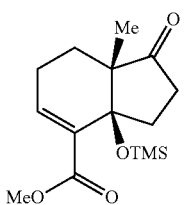
6
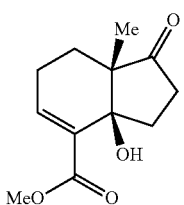
10
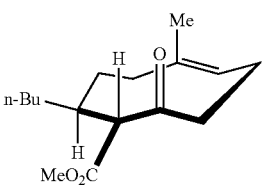
11b
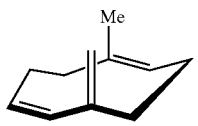
12
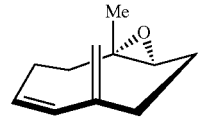
13
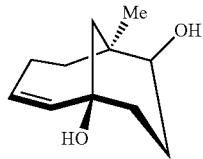
14
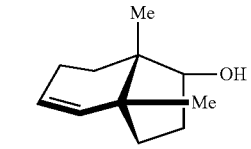
20

-continued

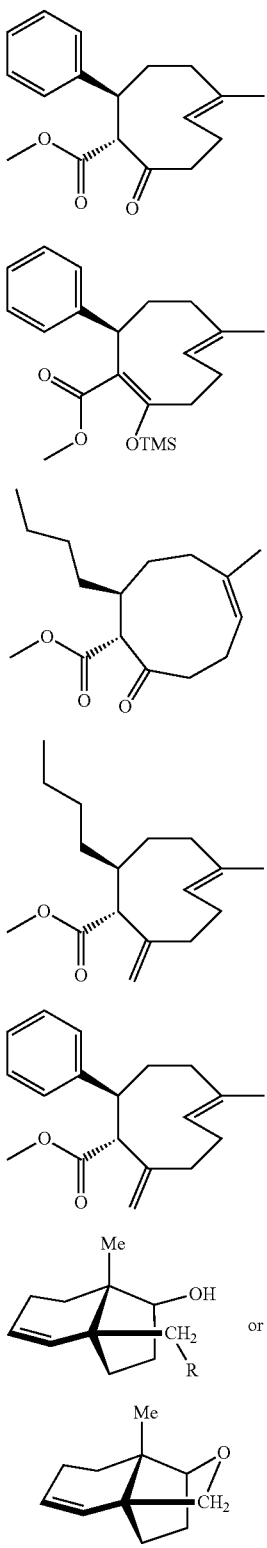

wherein:

$R^a$ is H, $(C_1-C_6)$alkyl, $(C_2-C_6)$alkenyl, $(C_2-C_6)$alkynyl, $(C_3-C_8)$cycloalkyl, $(C_3-C_8)$cycloalkyl$(C_1-C_6)$alkyl, aryl, or heteroaryl, wherein each $(C_1-C_6)$alkyl, $(C_2-C_6)$alkenyl, $(C_2-C_6)$alkynyl, $(C_3-C_8)$cycloalkyl, and $(C_3-C_8)$cycloalkyl$(C_1-C_6)$alkyl of $R^a$ is optionally substituted with one or more groups independently selected from halo, hydroxy, cyano, nitro, $(C_1-C_6)$alkoxy, $(C_3-C_8)$cycloalkyl, oxo, carboxy, aryl, aryloxy, and $-NR^bR^c$; and wherein each aryl, and heteroaryl of $R^a$ is optionally substituted with one or more groups independently selected from $(C_1-C_6)$alkyl, halo, hydroxy, cyano, carboxy, nitro, trifluoromethyl, trifluoromethoxy, $(C_1-C_6)$alkoxy, $(C_1-C_6)$alkoxycarbonyl, $(C_1-C_6)$alkanoyloxy, and $-NR^bR^c$; and $R^b$ and $R^c$ are each independently selected from H, $(C_1-C_6)$alkyl, $(C_3-C_8)$cycloalkyl, $(C_3-C_8)$cycloalkyl$(C_1-C_6)$alkyl, aryl, heteroaryl, aryl$(C_1-C_6)$ alkyl and heteroaryl$(C_1-C_6)$alkyl; or $R^b$ and $R^c$ together with the nitrogen to which they are attached form a aziridino, azetidino, morpholino, piperazino, pyrrolidino or piperidino; and $R^d$ is a hydroxy protecting group;

or a salt thereof. The compounds of formulae 1, 2, 3, 4, 4a, 4b, 4c, 4d, 5, 6, 10, 11, 11a, 11b, 12, 13, 14, 20, 23, 24, 25, 26, 27, 30, and 31 are useful as synthetic intermediates for preparing xenicane compounds and derivatives. As used herein TMS is trimethylsilyl.

In another embodiment the invention provides a method for preparing an epoxide of formula 12:

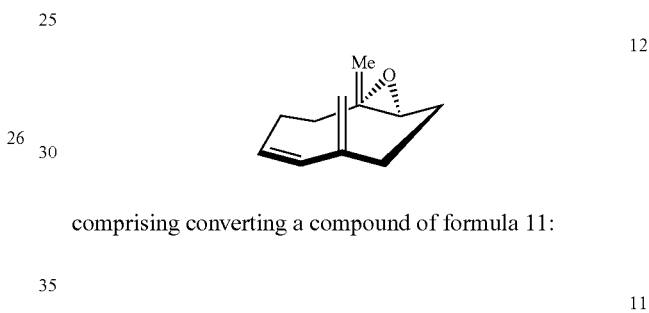

comprising converting a compound of formula 11:

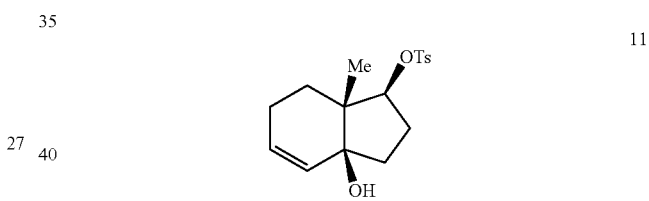

to the epoxide of formula 12.

In another embodiment the invention provides a method for preparing a methylene compound of formula 11b:

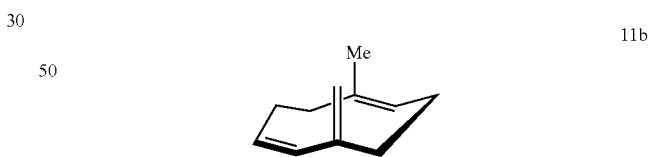

comprising converting a compound of formula 11a:

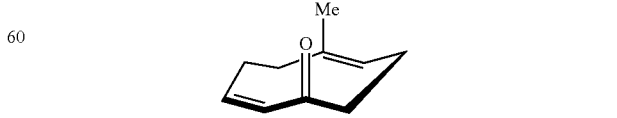

to the compound of formula 11b.

In another embodiment the invention provides a method for preparing a compound of formula 12:

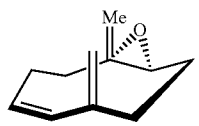

comprising converting a compound of formula 11b:

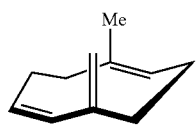

to the compound of formula 12.

In another embodiment the invention provides a method for preparing a compound of formula 13:

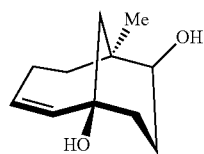

comprising converting a compound of formula 12:

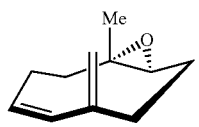

to the compound of formula 13.

In another embodiment the invention provides a method for preparing a compound of formula 14:

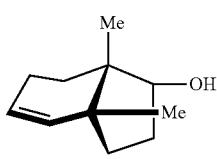

comprising converting a compound of formula 12:

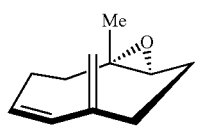

to the compound of formula 14.

The invention also provides novel synthetic intermediates and synthetic methods described herein that are useful for preparing Xenicane compounds and derivatives.

Certain compounds of the invention (e.g. compound 13, 20, 26, or 27) may also possess beneficial biological properties similar to those possessed by known members of the Xenicane family (e.g. anti-cancer properties). Accordingly, in one embodiment the invention provides a method to treat cancer in an animal (e.g. a mammal) comprising administering a compound of the invention, or a pharmaceutically acceptable salt thereof, to the animal.

BRIEF DESCRIPTION OF THE FIGURE

FIG. 1: illustrates representative members of the Xenicane family.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents. Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$ alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; $(C_3-C_8)$cycloalkyl can be cyclopropyl, cyclobutyl, cyclopentyl, cyclohexyl, cycloheptyl, or cyclooctyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

"Protecting group" refers to a moiety of a compound that masks or alters the properties of a functional group or the properties of the compound as a whole. Chemical protecting groups and strategies for protection/deprotection are well known in the art. See e.g., *Greene's Protective Groups in Organic Synthesis*, Peter G. M. Wuts and Theodora W. Greene, John Wiley & Sons, Inc., New York, 2007. Protecting groups are often utilized to mask the reactivity of certain functional groups, to assist in the efficiency of desired chemical reactions, e.g., making and breaking chemical bonds in an ordered and planned fashion. Chemically protected intermediates may themselves be biologically active or inactive. Specific protecting groups include benzyl (Bn), para-methoxybenzyl, trimethylsilyl, triethylsilyl, and fluorobenzyl.

In cases where compounds are sufficiently basic or acidic, a salt of a compound can be useful as an intermediate for isolation or purification of the compound. Accordingly, the invention also provides salts of the compounds described herein. Additionally, administration of a compound of the invention as a pharmaceutically acceptable acid or base salt may be appropriate.

In one embodiment the invention provides a method for preparing an ester of formula 1:

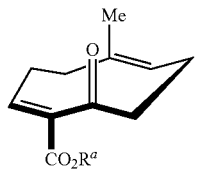

1 wherein $R^a$ is H, $(C_1-C_6)$alkyl, $(C_2-C_6)$alkenyl, $(C_2-C_6)$alkynyl, $(C_3-C_8)$cycloalkyl, $(C_3-C_8)$cycloalkyl$(C_1-C_6)$alkyl, aryl, or heteroaryl, wherein each $(C_1-C_6)$alkyl, $(C_2-C_6)$alkenyl, $(C_2-C_6)$alkynyl, $(C_3-C_8)$cycloalkyl, and $(C_3-C_8)$cycloalkyl$(C_1-C_6)$alkyl of $R^a$ is optionally substituted with one or more groups independently selected from halo, hydroxy, cyano, nitro, $(C_1-C_6)$alkoxy, $(C_3-C_8)$cycloalkyl, oxo, carboxy, aryl, aryloxy, and $-NR^bR^c$; and wherein each aryl, and heteroaryl of $R^a$ is optionally substituted with one or more groups independently selected from $(C_1-C_6)$alkyl, halo, hydroxy, cyano, carboxy, nitro, trifluoromethyl, trifluoromethoxy, $(C_1-C_6)$alkoxy, $(C_1-C_6)$alkoxycarbonyl, $(C_1-C_6)$alkanoyloxy, and $-NR^bR^c$; and $R^b$ and $R^c$ are each independently selected from H, $(C_1-C_6)$alkyl, $(C_3-C_8)$cycloalkyl, $(C_3-C_8)$cycloalkyl$(C_1-C_6)$alkyl, aryl, heteroaryl, aryl$(C_1-C_6)$ alkyl and heteroaryl$(C_1-C_6)$alkyl; or $R^b$ and $R^c$ together with the nitrogen to which they are attached form a aziridino, azetidino, morpholino, piperazino, pyrrolidino or piperidino;

comprising converting an acid of formula 2:

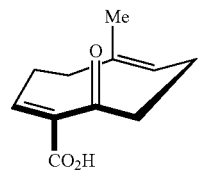

2 to the ester of formula 1. This conversion can be carried out by esterifying the acid of formula 2 under any suitable conditions. The conversion can be carried out at any suitable temperature (e.g. a temperature in the range of about −20° C. to about 150. The conversion can also be carried out in the presence of a suitable solvent (e.g. a polar organic solvent such as one comprising methanol, ethanol, propanol, isopropanol, butanol, isobutanol, sec-butanol, pentanol, hexanol or a mixture thereof). Any suitable source for the group $R^a$ can be used for this conversion as can any suitable carboxylic acid derivative, e.g. an active ester like a mixed anhydride, etc. When $R^a$ is a methyl group, suitable sources include $(Me)_3SiCHN_2$. In one embodiment of the invention, this conversion can be carried out by treating the acid of formula 2 with $(Me)_3SiCHN_2$ in methanol at about 0° C.

In one embodiment the invention provides a method for preparing an acid of formula 2 from a compound of formula 3:

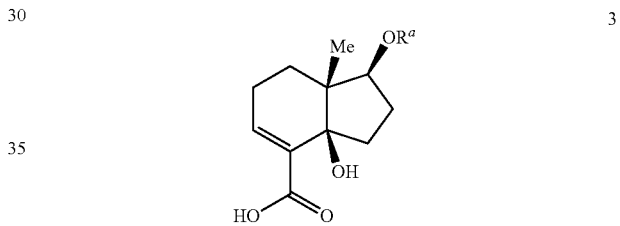

3 wherein $R^a$ is para-toluenesulfonyl. This conversion can be carried out under any suitable C—C fragmentation conditions. For example, this conversion can be carried out by treatment of the compound of formula 3 with a suitable base (e.g. NaH, t-BuOK, t-BuONa, dimsyl sodium, etc. The conversion can be carried out at any suitable temperature (e.g. a temperature in the range of about −78° C. to about 150. The conversion can also be carried out in the presence of a suitable solvent (e.g. a polar organic solvent such as dimethylformamide, dimethyl sulfoxide, hexamethylphosphoramide, or a mixture thereof). In one embodiment of the invention, this conversion can be carried out by treating the compound of formula 3 with NaH in HMPA at about 0° C.

In one embodiment the invention provides a method for preparing a compound of formula 3 from a compound of formula 4:

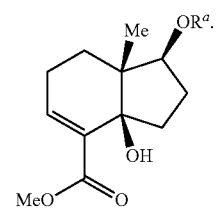

4 wherein R^a is para-toluenesulfonyl. This conversion can be carried out by hydrolyzing the ester of formula 4 under any suitable conditions. For example, this conversion can be carried out by treating the ester of formula 4 with a base (e.g. a hydroxide salt such as potassium hydroxide). The conversion can be carried out at any suitable temperature (e.g. a temperature in the range of about 0° C. to about 100° C. The conversion can also be carried out in the presence of a suitable solvent (e.g. an organic solvent such as tetrahydrofuran, methanol, ethanol, ethylene glycol or a mixture thereof). In one embodiment of the invention this conversion can be carried out by treating the ester of formula 4 with potassium hydroxide in tetrahydrofuran at about 20° C. Importantly, compound 4 does not readily undergo C—C fragmentation to give compound 1 (where R^a=methyl), and remarkably fragmentation conditions that effect C—C fragmentation of the des-carboalkoxy analogue fails for this substrate.

In one embodiment the invention provides a method for preparing a compound of formula 4 from a compound of formula 5:

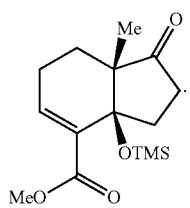

5

This conversion can be carried out in three steps. First the ketone in the compound of formula 5 can be reduced to the corresponding alcohol of formula 4a:

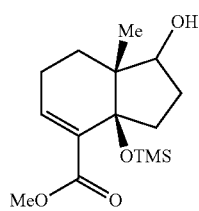

4a

This reduction can be carried out under any suitable conditions. The reduction can be carried out at any suitable temperature (e.g. a temperature in the range of about −78° C. to about 100. The reduction can also be carried out in the presence of a suitable solvent (e.g. an organic solvent such as one comprising methanol, tetrahydrofuran, diethyl ether, toluene, or a mixture thereof). Any suitable reducing agent can be used for this conversion (e.g. sodium borohydride, sodium triethylborohydride, or n-Bu-CBS/BH_3.SMe_2). In one embodiment of the invention this reduction can be carried out by treating the ketone of formula 5 with sodium borohydride in a solvent comprising methanol and tetrahydrofuran at about 20° C. The alcohol 4a resulting from the reduction can then be protected under any suitable conditions with any suitable protecting group under standard conditions to provide the corresponding protected alcohol. In one embodiment of the invention, this protection can be carried out by treating the alcohol with tosyl chloride in the presence of a suitable base (e.g. 1,4-diazobicyclo[2.2.2]octane) at about 20° C. to provide a compound of formula 4b:

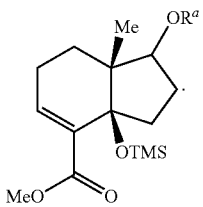

4b wherein R^a is para-toluenesulfonyl. The TMS group can be removed under any suitable conditions to provide the alcohol of formula 4. In one embodiment of the invention, the TMS group can be removed by treating with tetrabutyl-ammonium fluoride in tetrahydrofuran at about 20° C. (as mentioned above, compounds of type 4b may not undergo C—C fragmentation to give 1 (where R^a=methyl) under standard reaction conditions).

In one embodiment the invention provides a method for preparing a compound of formula 5 from a compound of formula 6:

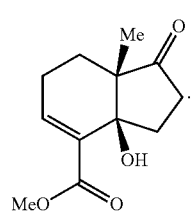

6

This conversion can be carried out by treatment of the compound of formula 6 under conditions that are suitable to introduce the trimethylsilyl group. In one embodiment of the invention, this conversion can be carried out by treating the compound of formula 6 with trimethylsilyl imidazole, neat, at about 20° C.

In one embodiment the invention provides a method for preparing a compound of formula 6 from a compound of formula 7:

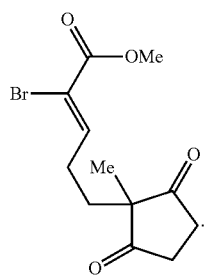

7

This conversion can be carried out under any suitable basic or organometallic conditions, e.g. Nozaki-Hiyama-Kishi, Barbier, or Grignard coupling conditions at any suitable temperature (e.g. a temperature in the range of about −78° C. to about 50° C. The conversion can also be carried out in the presence of a suitable solvent (e.g. a solvent such as dimethylformamide, dimethylsulfoxide, tetrahydrofuran, or diethyl ether, or a mixture thereof). In one embodiment of the invention, this conversion can be carried out by treating the compound of formula 7 with CrCl_2 and NiCl_2 in dimethylformamide in the presence or 4-angstrom molecular sieves at a temperature in the range of about 0° C. to about 20° C.

In one embodiment the invention provides a method for preparing a compound of formula 7 from a compound of formula 8:

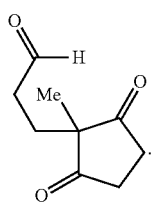

8

This conversion can be carried out under any suitable bromo-Wittig olefination conditions (see for example D. Chapdelaine, J. Belzile, P. Deslongchamps. *J. Org. Chem.* 2002, 67, 5669-5672). For example, this conversion can be carried out by treatment of the aldehyde 8 with a reagent of formula Br—C(=PPh$_3$)CO$_2$Me at any suitable temperature (e.g. a temperature in the range of about −78° C. to about 80° C.), in the presence of a suitable solvent (e.g. an organic solvent such as dichloromethane, chloroform, benzene, toluene, tetrahydrofuran, methanol, ethanol, dimethylformamide, or a mixture thereof), in the presence of a suitable base (e.g. an organic base or an inorganic base such as triethylamine, diethylisopropylamine, or potassium carbonate. In one embodiment of the invention, this conversion can be carried out by treating the aldehyde 8 with HC(=PPh$_3$)CO$_2$Me and N-bromosuccinimide in dichloromethane in the presence of potassium carbonate at a temperature from about −20° C. to about 20° C.

In one embodiment the invention provides a method for preparing a compound of formula 8 from a compound of formula 9:

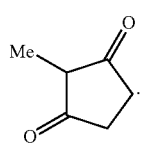

9

This conversion can be carried out under any suitable Michael addition conditions (see for example R. R. Huddleston, M. J. Krische. *Org. Lett.* 2003, 5, 1143-1146). For example, this conversion can be carried out by treatment of the diketone 9 with acrolein at any suitable temperature (e.g. a temperature in the range of about −20° C. to about 110° C., in the presence of a suitable solvent (e.g. water, methanol, acetonitrile, tetrahydrofuran, diethyl ether, ethyl acetate, or toluene, or a mixture thereof), in the presence of a suitable acid (e.g. an organic acid or base such as acetic acid or triethylamine. In one embodiment of the invention, this conversion can be carried out by treating the diketone 9 with acrolein in water in the presence of acetic acid at a temperature of about 20° C.

In one embodiment the invention provides a method for preparing an epoxide of formula 12:

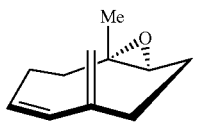

12 comprising converting a compound of formula 11:

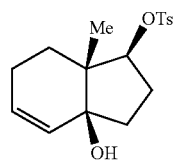

11 to the compound of formula 12. The epoxide of formula 12 is a useful synthetic intermediate that can be used to prepare members of the xenicane compound family. This conversion can conveniently be carried out by treating the alcohol 11 with a suitable base (e.g. sodium hydride, sodium cyanoborohydride, zinc borohydride, diisobutyl aluminum hydride, and related reagents, sodium in ammonia, or sodium naphthylide and related dissolving metal reducing agents,) in a suitable solvent (e.g. dimethylformamide, tetrahydrofuran, ether, ammonia, methylene chloride and related halogenated solvents, or a mixture thereof) at a suitable temperature (e.g. a temperature in the range of from about −20° C. to about 50° C.) to form the ketone of formula 11a:

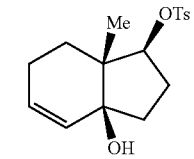

11a

The ketone of formula 11a can then be converted to the corresponding methylene compound of formula 11b:

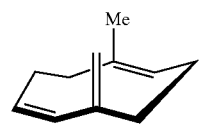

11b

This conversion can conveniently be carried out by treating the ketone with a suitable methylene forming reagent (e.g. Wittig reagents (e.g. Ph3PCH2), Peterson olefination reagents (TMSCH2Li), Tebbe olefination reagents (C$_5$H$_5$)$_2$ TiCH$_2$ClAl(CH$_3$)$_2$) and related phosphines, and silyl and titanium reagents. For example this conversion can be carried out in a suitable solvent (e.g. toluene, pyridine, benzene, 2,6-lutidine, THF, or ether, or a mixture thereof) at any suitable temperature (e.g. a temperature in the range of from about −20° C. to about 50° C.) to form the methylene compound of formula 11b.

Epoxidation of the compound of formula 11b provides the compound of formula 12. This conversion can conveniently be carried out by treating the compound of formula 11b with a suitable epoxidizing agent (e.g. mCPBA peroxyacetic acid, trifluoroperacetic acid, DMDO and related dioxiranes, oxaziridines, oxaziridinium, or molybdenum dioxide reagents) in a suitable solvent (e.g. hexanes, toluene, benzene, methylene chloride, chloroform, carbon tetrachloride, methanol, or ethanol, or a mixture thereof) at any suitable temperature (e.g. a temperature in the range of from about −20° C. to about 50° C.) to form the methylene compound of formula 11b.

In one embodiment the invention provides a method for preparing a compound of formula 13:

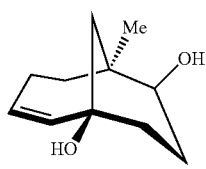

13 comprising converting a compound of formula 12:

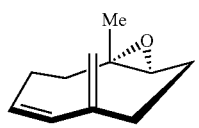

12 to the compound of formula 13. The compound of formula 13 is a useful synthetic intermediate that can be used to prepare members of the xenicane compound family, in particular, members of the florlide family of compounds. This conversion can conveniently be carried out by an acid catalyzed opening of the epoxide ring. For example, this conversion can be carried out by treating the compound of formula 12 with a BF$_3$.Et$_2$O (or another suitable reagent e.g. or BBr$_3$, AlCH$_3$Cl$_2$, CSA, TsOH, TiOiPr$_4$) in a suitable solvent (e.g. dichloromethane, ether, tetrahydrofuran, or toluene or a mixture thereof) at any suitable temperature (e.g. a temperature in the range of from about −100° C. to about 50° C.) to form the methylene compound of formula 13.

In one embodiment the invention provides a method for preparing a compound of formula 14:

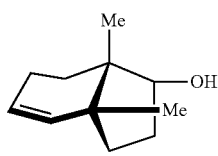

14 comprising converting a compound of formula 12 to the compound of formula 14. The compound of formula 14 is a useful synthetic intermediate that can be used to prepare members of the xenicane compound family, in particular, members of the xenibellol family of compounds. This conversion can conveniently be carried out by preparing Cp$_2$TiCl$_2$ and Zn dust in a suitable solvent (e.g. tetrahydrofuran, ether, dimethylformamide, HMPA, or dichloromethane, or a mixture thereof) at any suitable temperature (e.g. a temperature in the range of from about −20° C. to about 50° C.), followed by addition of treating the compound of formula 12 in a suitable solvent (e.g. tetrahydrofuran, ether, dimethylformamide, HMPA, or dichloromethane, or a mixture thereof) to form the compound of formula 14.

In one embodiment the invention provides a method for preparing a compound of formula 30:

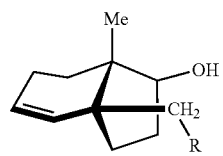

30 wherein R is halo, a nitrogen-linked group, an oxygen-linked group, a carbon-linked group, or a group that is linked through a carbonyl group, comprising converting a compound of formula 12 to the compound of formula 30. The compound of formula 30 is a useful synthetic intermediate that can be used to prepare members of the xenicane compound family. This conversion can conveniently be carried out treating the compound of formula 12 with Cp$_2$TiCl$_2$ and Zn dust in a suitable solvent (e.g. tetrahydrofuran) at any suitable temperature (e.g. a temperature in the range of from about −20° C. to about 50° C.) to provide an intermediate titanium compound and treating the intermediate titanium compound with an electrophilic source of R to provide the compound of formula 30. See for example W. A. Nugent, T. V. RajanBabu. *J. Am. Chem. Soc.* 1988, 110, 8561-8562. When R is Cl, N-chlorosuccinimide is a suitable source of Cl. In one embodiment of the invention R is halo, amino, (C$_1$-C$_6$)alkylamino, di(C$_1$-C$_6$)alkylamino, (C$_1$-C$_6$)alkyl, (C$_1$-C$_6$)alkoxy, or (C$_1$-C$_6$)alkanoyl.

In one embodiment the invention provides a method for preparing a compound of formula 31:

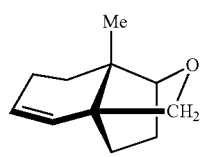

31 comprising converting a compound of formula 30 wherein R is a suitable leaving group (e.g. Cl, Br, or I) to the compound of formula 31. The compound of formula 31 is a useful synthetic intermediate that can be used to prepare members of the xenicane compound family. This conversion can conveniently be carried out treating the compound of formula 31 with a suitable base (e.g. sodium hydride) in a suitable solvent (e.g. tetrahydrofuran) at any suitable temperature (e.g. a temperature in the range of from about −20° C. to about 50° C.) to provide the compound of formula 31.

The ester of formula 1 is a versatile intermediate that can be transformed into a variety of structurally diverse xenicane compounds. For example, as illustrated below, the ester of formula 1 can be alkylated by treatment with an organocuprate reagent to give a the compound of formula 10 in high yield with high stereoselectivity. The compound of formula 10 is another useful intermediate that can be used to prepare xenicane compounds.

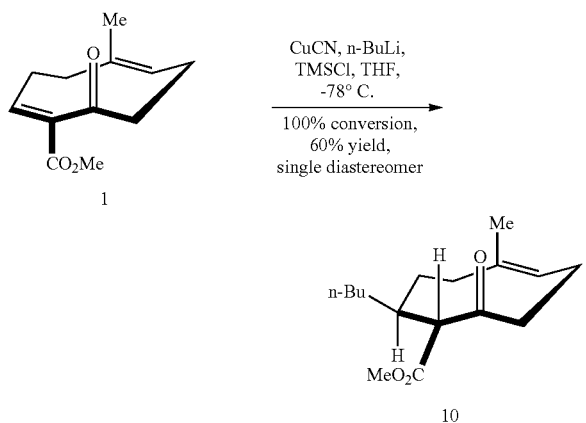

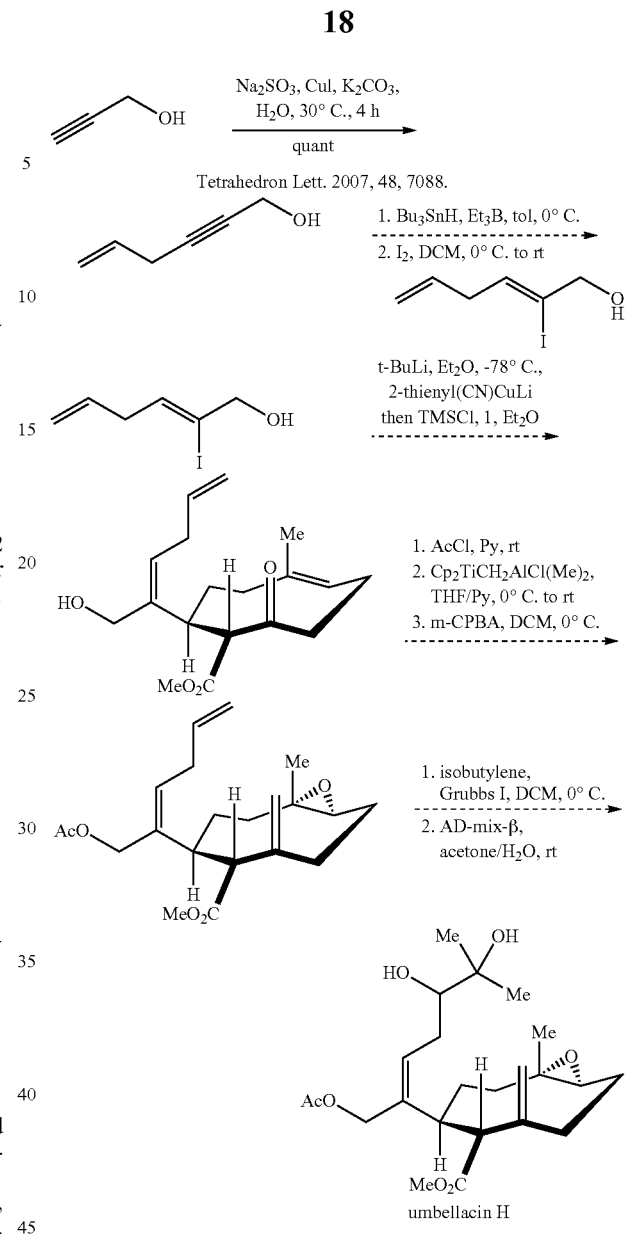

For comparison, as illustrated below, conversion of the acid 2 to a similar product 11 proceeds with a significantly lower yield. This comparison demonstrates the utility of the ester 1 as an intermediate for preparing xenicane compounds.

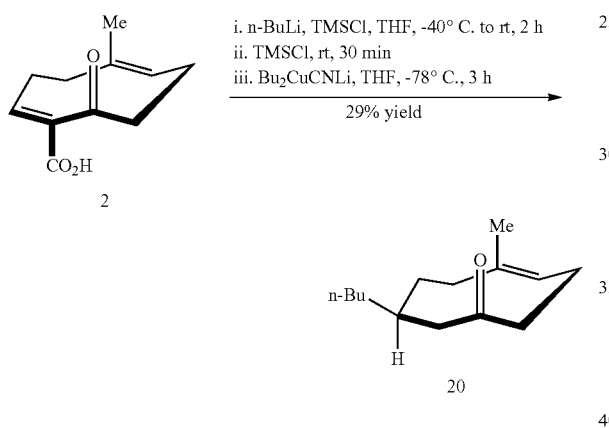

In one embodiment the invention also provides the compound of formula 11, which is also a useful intermediate for preparing xenicane compounds.

The global oncology market exceeds $50 billion annually, has grown faster than the pharmaceutical industry as a whole, and is expected to expand with increasing global demand for these medicines (forecasted revenues of $92 billion in 2012). The intermediates and methods of the invention can be used for producing novel terpenoids in sufficient quantities for drug discovery/development. These novel compounds are expected to possess useful biological activity, including, but not limited to, anticancer, antibiotic, antiviral, and antifungal properties.

The bioactive xenicanes are accessible only in miniscule quantities from natural sources. Currently known methods of isolation are impractical for a drug development program. The intermediates and methods of the invention can provide access to the mono-, bi-, and tricyclic congeners of the xeniolide, florlide, xenibellol, and related classes of xenicanes, respectively. With the bottleneck of availability removed, a variety of analogues can be produced for SAR studies.

The ester of formula 1 can be converted to a natural xenicane accordin to the scheme below. The target compound Umbellacin H was isolated from the soft coral *Xenia umbellata*, and exhibits cytotoxicity against murine P-388 lymphocytic leukemia with an $ED_{50}$ value 3.4 μg/mL (*J. Nat. Prod.* 2006, 69, 338).

The invention will now be illustrated by the following non-limiting Examples.

EXAMPLES

General Information: Starting materials, reagents, and solvents were purchased from commercial suppliers (Aldrich, Acros, Lancaster, and Fischer) and used as received unless otherwise noted. Water-sensitive reactions were conducted using anhydrous solvents in flame-dried glassware with magnetic stirring under an inert atmosphere of dry argon. Reaction progress was monitored by analytical thin layer chromatography (TLC), using 250 μm silica gel plates (Dynamic Absorbents F-254). Visualization was accomplished with UV light and anisaldehyde stain, followed by heating. Flash column chromatography (FCC) was conducted using 230-400 mesh, pore size 60 Å, Silicycle, ultra pure silica gel. Infrared (IR) spectra were recorded on an ATI Mattson Genesis Series FT-Infrared spectrophotometer. Proton nuclear magnetic resonance ($^1$H NMR) spectra were recorded on either a Varian-300 instrument (300 MHz), Varian-400 instrument (400 MHz), Varian-500 instrument (500 MHz), or a Varian-600 instrument (600 MHz). Chemical shifts are reported in ppm relative to tetramethylsilane (TMS) as the internal standard. Data are reported as follows: chemical shift, integration, multiplicity (s=singlet, d=doublet, t=triplet, q=quartet, br=broad, m=multiplet), and coupling constants (Hz). Carbon nuclear magnetic resonance ($^{13}$C NMR) spectra were recorded on either a Varian-300 instrument (75 MHz), Varian-400 instrument (100 MHz), Varian-500 instrument (125 MHz), or Varian-600 instrument (150 MHz). Chemical shifts are reported in ppm relative to tetramethylsilane (TMS) as the internal standard. Mass spectra were recorded on a Finnigan LCQ-DUO mass spectrometer.

Example 1

Preparation of Compound 8 from Compound 9

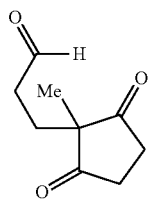

To a vigorously stirred suspension of 2-methyl-1,3-cyclopentanedione (9, 20.0 g, 175 mmol) in water (100 mL) was added acetic acid (0.520 mL, 9.09 mmol) and acrolein (19.5 mL, 262 mmol) at room temperature. After 2.5 hours, the suspension had turned into a clear yellow aqueous solution, which was concentrated under reduced pressure at 50° C. to a volume of about 10 mL. The product was extracted with excess ethyl acetate (50 mL×6). The combined organic phases were dried over sodium sulfate, filtered, and concentrated under reduced pressure to give the desired aldehyde (8, $R_f$ 0.4 in 1:1 EtOAc/hex, 29.4 g, 175 mmol, 100%) as a yellow oil. ESI-MS [M+H]$^+$ m/z calcd 169.2, observed 169.2.

Example 2

Preparation of Compound 7 from Compound 8

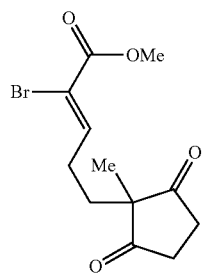

To a solution of N-bromosuccinimide (12.8 g, 71.3 mmol) in 110 mL of dichloromethane at −20° C. was added methyl (triphenylphosphoranylidene)acetate (12.2 g, 35.7 mmol) in one portion. The yellow solution turned into an orange suspension as it was allowed to gradually warm to room temperature. After 2.5 hours the suspension was cooled to 0° C., then a solution of 8 (5.00 g, 29.7 mmol, azeotroped×3 with excess toluene) in dichloromethane (40 mL) was added dropwise, followed by the addition of anhydrous potassium carbonate (10.4 g, 74.3 mmol). The reaction mixture was allowed to gradually warm to room temperature. After 20 hours, the brown suspension was filtered through Celite and flushed through with liberal amounts of dichloromethane. The filtrate was concentrated under reduced pressure, then the dark brown residue was purified by FCC (thin layer of Florisil underneath sand, 0 to 35% EtOAc/hex), yielding the desired vinyl bromide (7, $R_f$ 0.55 in 1:1 EtOAc/hex, 7.15 g, 23.59 mmol, 79%, 6:1 ratio of Z/E isomers) as a pale yellow oil. ESI-MS [M+H]$^+$ m/z calcd 303.2, observed 303.0.

Example 3

Preparation of Compound 6 from Compound 7

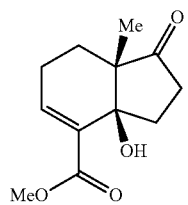

Dimethylformamide (165 mL) was placed over activated 4-angstrom powdered molecular sieves and degassed with dry argon for 30 minutes. 30 mL was syringed out and stored for future addition of starting material. Under an inert atmosphere of dry argon, chromium dichloride (4.27 g, 33.0 mmol) and nickel dichloride (0.044 g, 0.33 mmol) were weighed out and transferred into the 135 mL of degassed solvent. To this stirring light green suspension at 0° C. was added dropwise a solution of 7 (2.00 g, 6.60 mmol, azeotroped×3 with excess toluene) in dimethylformamide (10 mL). Two rinses of 10 mL each were subsequently added to ensure complete transfer. The reaction was allowed to gradually warm to room temperature. After 9 hours, the dark green suspension was vacuum filtered over Celite and flushed through with liberal amounts of ethyl acetate. The green filtrate was partitioned between brine (100 mL) and ethyl acetate/hexane (1:1, 150 mL). The aqueous layer was extracted twice more with equal volumes of ethyl acetate/hexane. The combined organic phases were washed with brine (25 mL), dried over sodium sulfate, filtered, and concentrated under reduced pressure at 50° C. The colorless oily residue was purified by FCC (0 to 17% EtOAc/hex), furnishing the desired alcohol (6, $R_f$ 0.5 in 5:1 EtOAc/hex×3, 1.20 g, 5.33 mmol, 81%) as a colorless oil. ESI-MS [M+Na]$^+$ m/z calcd 247.2, observed 247.1.

Example 4

Preparation of Compound 5 from Compound 6

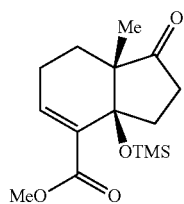

5

N-(Trimethylsilyl)imidazole (0.876 mL, 5.79 mmol) was added dropwise to 6 (0.433 g, 1.93 mmol) at room temperature. The yellow solution was stirred neat for 18 hours, then cooled to 0° C. Saturated aqueous ammonium chloride (10 mL) was added, and the product was extracted with dichloromethane (10 mL×3). The combined organic phases were dried over sodium sulfate, filtered, and concentrated under reduced pressure. Purification of the orange residue via FCC (0 to 17% EtOAc/hex) gave the desired TMS ether (5, $R_f$ 0.5 in 5:1 EtOAc/hex, 0.559 g, 1.89 mmol, 98%) as a colorless oil. ESI-MS [M+Na]$^+$ m/z calcd 319.4, observed 319.2.

Example 5

Preparation of Compound 4 from Compound 5

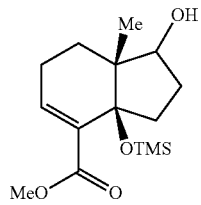

4a

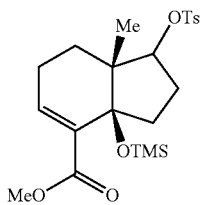

4b

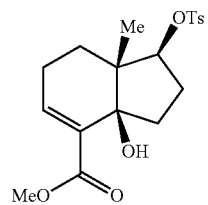

4

To a solution of 5 (0.640 g, 2.16 mmol) in tetrahydrofuran/methanol (9:1, 43 mL) at room temperature was added sodium borohydride (0.408 g, 10.8 mmol) in a single portion. All bubbling ceased after 10 minutes. The colorless reaction solution was diluted with diethyl ether (50 mL). Saturated aqueous ammonium chloride (10 mL) was added, and the product mixture was poured over brine (30 mL). The organic phase was separated, and the aqueous layer was washed with two more portions of diethyl ether (20 mL). The combined organic phases were dried over sodium sulfate, filtered, and concentrated under reduced pressure, yielding alcohol 4a ($R_f$ 0.15 in 17% EtOAc/hex, 0.644 g, 2.16 mmol, 100%, 1.4:1 ratio of α/β diastereomers) as a pale yellow oil. The diastereomers were inseparable by flash chromatography at this stage. Minor β diastereomer: $^1$H NMR (500 MHz, CDCl$_3$) δ 6.81 (t, J=4.0 Hz, 1H), 3.74 (s, 3H), 1.03 (s, 3H), 0.08 (s, 9H) ppm; ESIMS m/z 279.3 (M–H$_2$O$^+$). Major α diastereomer: $^1$H NMR (500 MHz, CDCl$_3$) δ 6.61 (t, J=2.3 Hz, 1H), 4.20 (t, J=8.3 Hz, 1H), 3.72 (s, 3H), 0.98 (s, 3H), 0.09 (s, 9H) ppm; ESIMS m/z 279.3 (M–H$_2$O$^+$).

To a solution of the diastereomeric alcohols (azeotroped×3 with excess toluene) in dichloromethane (21.9 mL) at room temperature was added 1,4-diazabicyclo[2.2.2]octane (0.726 g, 6.46 mmol) followed by p-toluenesulfonyl chloride (0.499 g, 2.58 mmol). Within 10 minutes, the clear yellow solution turned to a cloudy yellow suspension. After 20 hours, triethylamine (0.911 mL, 6.47 mmol) and more p-toluenesulfonyl chloride (0.8 equivalents) were added, then the suspension was concentrated under reduced pressure at 35° C. to push the reaction to completion. The product mixture was diluted with dichloromethane (50 mL) and washed with brine (10 mL×3). The combined organic phases were dried over sodium sulfate, filtered, and concentrated under reduced pressure, giving the crude tosylate 4b ($R_f$ 0.5 in 0.5 in 5:1 hex/EtOAc, 1.4:1 ratio of a/β diastereomers). To a beige suspension of the diastereomeric tosylates in tetrahydrofuran (21.9 mL) at room temperature was added tetrabutylammonium fluoride (1 M in THF, 2.37 mL, 2.37 mmol). After 24 hours, saturated aqueous ammonium chloride (10 mL) was added, and the products were extracted with diethyl ether (10 mL×3). The combined organic phases were washed with brine (5 mL), dried over sodium sulfate, filtered, and concentrated under reduced pressure. The crude dark yellow oily residue was purified by FCC (0 to 17% EtOAc/hex), affording the undesired a tosylate ($R_f$ 0.4 in 5:1 hex/EtOAc×3, 0.491 g, 1.29 mmol, 60%) as a colorless oil and the desired (3 tosylate (4, $R_f$ 0.3 in 5:1 hex/EtOAc×3, 0.304 g, 0.799 mmol, 37%) as a colorless oil. ESI-MS [M+Na]$^+$ m/z calcd 475.6, observed 474.8.

Example 6

Preparation of Compound 3 from Compound 4

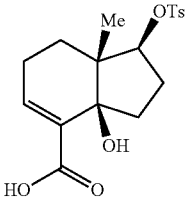

3

To a vigorously stirred solution of 4 (0.192 g, 0.505 mmol) in tetrahydrofuran (4 mL) at room temperature was added potassium hydroxide (1 M in water, 5.05 mL, 5.05 mmol). After 5 hours, the biphasic reaction contents were partitioned between brine (5 mL) and diethyl ether (5 mL). The basic aqueous phase was separated, washed with diethyl ether (1 mL×2), and carefully acidified to pH 1 with 1 N hydrochloric acid. The product was extracted with diethyl ether (15 mL×3). The combined organic phases were dried over sodium sulfate, filtered, and concentrated under reduced pressure, furnishing the desired acid (3, $R_f$ 0.2 in 1:1 hex/EtOAc, 0.180 g, 0.491 mmol, 97%) as a colorless foamy solid. IR (thin film) 3479, 3065, 2929, 1703, 1698, 1693, 1682, 1355, 1189, 1175, 971, 668, 557 cm$^{-1}$; $^1$H NMR (400 MHz, CDCl$_3$) δ 7.79 (d, J=8.2 Hz, 2H), 7.33 (d, J=8.1 Hz, 2H), 7.03 (t, J=3.8 Hz, 1H), 4.53 (t, J=6.5 Hz, 1H), 3.76 (br s, 1H), 2.44 (s, 3H), 2.37-2.09 (m, 3H), 2.06-1.94 (m, 2H), 1.93-1.80 (m, 1H), 1.51-1.39 (m, 2H), 1.02 (s, 3H) ppm; $^{13}$C NMR (100 MHz, CDCl$_3$) δ 170.9, 144.8, 142.5, 134.4, 133.0, 129.9, 127.9, 87.2, 78.6, 47.9, 37.8, 30.0, 28.8, 23.1, 21.8, 14.5 ppm; ESIMS m/z 365.1 (M−H$^-$).

Example 7

Preparation of Compounds 1 and 2

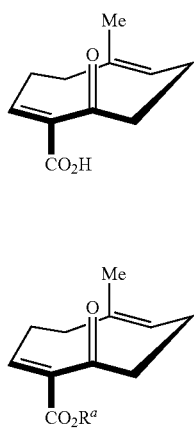

To a solution of 3 (0.284 g, 0.775 mmol) in hexamethylphosphoramide (5 mL) at 0° C. was added sodium hydride (60% in mineral oil, rinsed with hexane, 0.155 g, 3.88 mmol) portionwise in hexamethylphosphoramide. The reaction solution immediately turned into a cloudy yellow suspension. A miniature workup was required on each reaction aliquot in order to monitor fragmentation progress by TLC. The suspension turned brown within 5 minutes, then saturated aqueous ammonium chloride (5 mL) was added dropwise. The basic aqueous phase was washed with diethyl ether (3 mL×3), and carefully acidified to pH 1 with 1 N hydrochloric acid, turning the dark yellow solution into a cloudy pale yellow suspension. The product was extracted with diethyl ether (10 mL×3). The combined organic phases were backwashed with brine (5 mL×3), dried over sodium sulfate, filtered, and concentrated under reduced pressure, giving a crude yellow solution of acid 2 ($R_f$ 0.4 in 1:1 hex/EtOAc) in trace hexamethylphosphoramide. The crude product (azeotroped×3 with excess toluene) was diluted with methanol (7.75 mL). To this solution at 0° C. was added trimethylsilyldiazomethane (2.0 M in diethyl ether, 0.388 mL, 0.775 mmol) dropwise. After 30 minutes, more trimethylsilyldiazomethane was added dropwise in increments of 0.1 equivalents until complete consumption of starting material was observed by TLC. The solvent was removed under reduced pressure, and the yellow oily residue was purified by FCC (0 to 10% EtOAc/hex), yielding the desired ester (1, $R_f$ 0.4 in 5:1 hex/EtOAc, 0.078 g, 0.375 mmol, 48%) as a colorless oil. Where $R^a$=Me; ESI-MS [M+H]$^+$ m/z calcd 209.1, observed 209.1. ESI-MS [M+H$_2$O]$^+$ m/z calcd 226.0, observed 226.0. ESI-MS [M+Na]$^+$ m/z calcd 231.0, observed 231.0.

Compound 2 can also be prepared as follows.

To a solution of acid-tosylate 3 (0.546 g, 1.490 mmol) in HMPA (previously dried over 4 Å molecular sieves, 9.93 mL) at 0° C. was added sodium hydride (60% in mineral oil, 0.298 g, 7.450 mmol), producing a brown suspension. After 1 h, brine (10 mL) was added dropwise at 0° C. until the evolution of H$_2$ gas ceased. The basic aqueous mixture was washed with DCM (removing mineral oil, 4×5 mL). The combined organic layers were back-extracted with 1M aq KOH (2 mL). The combined aqueous layers were carefully acidified to pH 1 with 1N HCl. The product was extracted from the acidic aqueous phase with small volumes of Et$_2$O. The combined organic layers were diluted with Et$_2$O to a volume of ~50 mL, washed with brine (3×2 mL), dried over Na$_2$SO$_4$, filtered, and concentrated under reduced pressure, furnishing crude cyclononadienone-carboxylic acid 10 in trace HMPA as a pale yellow oil. To monitor this reaction by TLC, a miniature acid-base workup should be applied to every aliquot to remove as much HMPA as possible prior to spotting the plate. The $R_f$ values of 2 and 3 are indistinguishable by TLC. The only way to monitor this reaction is to judge the extent of the color change of the acid smear. In p-anisaldehyde, 3 stains green, and 2 stains black. If any green color is observed in the acid smear, the reaction is not complete. HMPA is difficult to remove completely from this polar product. For practical purposes the crude product should be used directly in the next step, since compound 2 is unstable on silica gel. By repeated brine washes and back-extractions, an analytical sample (8 mg) of pure 2 was secured as a colorless oil. IR (neat) 3126, 2937, 2861, 1698, 1682, 1384, 1278, 1161 cm$^{-1}$; $^1$H NMR (300 MHz, CDCl$_3$) δ 7.04 (t, J=8.7 Hz, 1H), 5.42 (dd, J=12.0, 2.1 Hz, 1H), 3.18 (td, J=11.5, 7.9 Hz, 1H), 2.70 (qd, J=11.9, 7.2 Hz, 1H), 2.46-2.25 (m, 3H), 2.24-2.12 (m, 2H), 1.83 (t, J=12.0 Hz, 1H), 1.60 (s, 3H) ppm; $^{13}$C NMR (75 MHz, CDCl$_3$) δ 203.9, 169.9, 147.1, 139.8, 134.9, 127.6, 44.1, 36.1, 26.1, 25.3, 16.7 ppm; ESIMS m/z 193.3 (M−H$^-$).

Compound 1 can also be prepared as follows.

To a yellow solution of crude cyclononadienone-carboxylic acid 2 (theoretical 0.289 g, 1.488 mmol) in DCM (14.9 mL) at rt was added MeOH (0.301 mL, 7.44 mmol), 4-dimethylaminopyridine (0.018 g, 0.149 mmol), and 1-ethyl-3-(3-dimethylaminopropyl)carbodiimide (0.299 mL, 1.637 mmol). After 2 h, brine (5 mL) was added dropwise, and the mixture was extracted with DCM (3×5 mL). The combined organic layers were washed with brine (5 mL), dried over Na$_2$SO$_4$, filtered, and concentrated under reduced pressure to a brown residue. Purification of the crude material by FCC (0 to 17% EtOAc/hexane) furnished cyclononadienone-carboxylate-methyl ester 1 (0.188 g, 61% over 2 steps) as a colorless oil. IR (neat) 2983, 2936, 2860, 1731, 1699, 1456, 1435, 1277, 1245, 1050, 666 cm$^{-1}$; 1H NMR (300 MHz, CDCl$_3$) δ 6.91 (t, J=8.7 Hz, 1H), 5.41 (dd, J=12.1, 2.2 Hz, 1H), 3.78 (s, 3H), 3.08 (td, J=11.6, 7.7 Hz, 1H), 2.79-2.59 (m, 1H), 2.53-2.23 (m, 3H), 2.22-2.11 (m, 2H), 1.80 (dd, J=17.5, 6.9 Hz, 1H), 1.59 (s, 3H) ppm; $^{13}$C NMR (125 MHz, CDCl$_3$) δ 204.2, 165.4, 144.2, 140.4, 134.9, 127.4, 52.3, 44.0, 36.1, 25.9, 25.3, 16.7 ppm; ESIMS m/z 209.1 (M+H$^+$), 226.0 (M+H$_2$O$^+$), 231.0 (M+Na$^+$); HPLC: Daicel Chiralpak AS-H,

Example 8

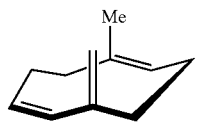

(aR)-2-methyl-7-methylidenecyclonona-(1E,5Z)-diene (11b)

To a solution of cyclononadienone 11a ($R_f$ 0.45 in 5:1 hex/EtOAc, 0.2453 g, 1.633 mmol, azeotroped×3 with excess toluene) in THF/pyridine (5:1, 63 mL) at 0° C. was added Tebbe reagent (0.5 M in toluene, 13.1 mL, 6.55 mmol) dropwise. The solution gradually turned from orange to reddish brown as the reaction was slowly warmed to room temperature. The starting material was completely consumed after 2 h. The reaction mixture was diluted with 50 mL of diethyl ether. 1 M aqueous NaOH was added dropwise at 0° C. until the evolution of gas ceased, giving a creamy orange/red suspension. The quenched mixture was filtered through Celite and flushed through with liberal amounts of diethyl ether. The orange filtrate was washed with brine (20 mL). The organic layer was dried over $Na_2SO_4$, filtered, and concentrated gently (rotovapped at no less than 50 torr at rt) to give an oily orange residue. The crude material was purified by FCC (100% hex). Leftover toluene was gently rotovapped off (no less than 50 torr at rt), giving the desired cyclononatriene 11b ($R_f$ 0.5 in 100% hex, 0.195 g, 1.315 mmol, 81%) as a volatile, colorless oil with a distinct terpene scent. Blowing a gentle stream of argon over a solution of the triene in toluene at −78° C. effects evaporation of this product. IR $v_{max}$ (neat)/cm$^{-1}$ 3073, 3046, 2994, 2926, 2854, 1453, 895, 759, 665. $^1$H NMR (CDCl$_3$, 500 MHz) δ 5.81 (1H, d, J=12.0 Hz), 5.24 (1H, ddd, J=12.0, 8.5, 7.5 Hz), 5.14 (1H, cld, J=10.5, 0.5 Hz), 4.62 (1H, br s), 4.58 (1H, br s), 2.42-2.27 (2H, m), 2.23 (1H, qt, J=11.0, 1.5 Hz), 2.10-1.97 (3H, m), 1.96-1.88 (2H, m), 1.53 (3H, s) ppm. $^{13}$C NMR (CDCl$_3$, 75 MHz) δ 146.9, 138.1, 133.9, 127.5, 126.0, 112.4, 39.8, 37.9, 28.4, 26.0, 17.6 ppm. ESI-MS [M+H]$^+$ m/z calcd 149.1, observed 149.2.

The starting material (aR)-6-methylcyclonona-(2Z,6E)-dienone (11a) was prepared according to published procedures Am. Chem. Soc. 2008, 130, 2954; Tetrahedron Lett., 2009, 50, 1882).

Example 9

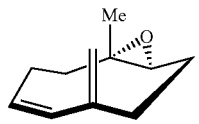

(aR)-(1S,9S)-1-methyl-6-methylidene-10-oxabicyclo[7.1.0]dec-(4Z)-ene (12)

To a solution of 11b ($R_f$ 0.5 in 100% hex, 0.0975 g, 0.658 mmol) in DCM (24 mL) at 0° C. was added m-CPBA (77% by mass, 0.147 g, 0.658 mmol). The colorless reaction solution was gradually warmed to room temperature over 2 h, quenched by the addition of saturated aq. $Na_2SO_3$ (5 mL), and extracted with DCM (3×10 mL). The combined organic layers were washed with brine (10 mL), dried over $Na_2SO_4$, filtered, and concentrated under reduced pressure to give an oily yellow residue. The crude product was purified by FCC (0 to 10% EtOAc/hex), furnishing the desired cyclononaepoxydiene 12 ($R_f$ 0.55 in 5:1 hex/EtOAc, 0.0941 g, 0.573 mmol, 87%) as a white crystalline solid with a distinct eucalyptus/menthol/camphor scent. IR $v_{max}$ (thin film)/cm$^{-1}$ 3074, 2956, 2918, 2849, 1726, 1463, 1379, 1262, 1073. $^1$H NMR (CDCl$_3$, 400 MHz) δ 5.89 (1H, d, J=11.5 Hz), 5.50 (1H, ddd, J=11.5, 9.0, 7.5 Hz), 4.99 (1H, br s), 4.95 (1H, br s), 3.13 (1H, dd, J=12.0 Hz, 2.0 Hz), 2.66-2.57 (1H, m), 2.47-2.39 (1H, m), 2.14-2.06 (2H, m), 2.05-1.94 (2H, m), 1.45 (1H, qd, J=11.5, 3.5 Hz), 1.29 (3H, s), 0.97-0.81 (3H, m) ppm. $^{13}$C NMR (CDCl$_3$, 75 MHz) δ 145.9, 137.3, 127.5, 114.1, 62.1, 60.0, 36.2, 31.7, 27.2, 21.6, 18.5 ppm. ESI-MS [M+H]$^+$ m/z calcd 165.1, observed 165.1.

Example 10

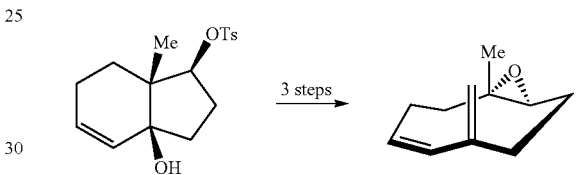

(aR)-(1S,9S)-1-methyl-6-methylidene-10-oxabicyclo[7.1.0]dec-(4Z)-ene (12)

Sodium hydride (60% in mineral oil, rinsed with hexane, 0.0244 g, 0.638 mmol) was added to a solution of enantioenriched tosyl alcohol 11 (87% ee, $R_f$ 0.1 in 5:1 hex/EtOAc, 0.153 g, 0.475 mmol, azeotroped×3 in toluene) in DMF (15 mL) at 0° C. The reaction mixture turned dark brown within 5 minutes, and was quenched after 2 h by the addition of cold brine (13 mL). The resulting mixture was extracted with cold diethyl ether (3×50 mL). The combined organic extracts were washed with cold brine (2×25 mL), dried over $Na_2SO_4$ (surrounded by an ice-water bath), filtered, and concentrated gently under reduced pressure at 0° C. (no less than 50 torr). The crude cyclononadienone 11a ($R_f$ 0.5 in 5:1 hex/EtOAc) was dissolved in cold toluene/pyridine (5:1, 15 mL) in the presence of freshly activated (then cooled under argon) 4 Å molecular sieves. To this solution at 0° C. was added Tebbe reagent (0.5 M in toluene, 3.796 mL, 1.898 mmol) dropwise, turning the reaction mixture orange then dark brown. After 2 h, the reaction was diluted with 40 mL of cold diethyl ether and quenched with cold 1 M aqueous NaOH until the evolution of gas ceased. The creamy orange/red suspension was filtered through Celite and flushed through with liberal amounts of cold diethyl ether. The orange filtrate was washed once with cold brine (50 mL). The organic layer was concentrated carefully under reduced pressure at 0° C. (no less than 30 torr) to give an oily orange residue. The crude material was quickly flushed through a cold silica gel plug with cold hexane and collected in a roundbottom flask surrounded by an ice-water bath. The purified cyclononatriene 11b ($R_f$ 0.5 in 100% hex) solution was concentrated to a volume of ~25 mL. To this solution at 0° C. was added m-CPBA (77% by mass, 0.0954 g in 0.010 mg increments, 0.428 mmol). The completed reaction was quenched by the addition of saturated aq. Na$_2$SO$_3$ (5 mL). After warming to rt, the product was extracted with DCM (3×20 mL). The combined organic layers were washed with brine (10 mL), dried over Na$_2$SO$_4$, filtered, and concentrated under reduced pressure to give an oily yellow residue. The crude material was purified by FCC (0 to 10% EtOAc/hex), furnishing the desired cyclononaepoxydiene 12 (R$_f$ 0.55 in 5:1 hex/EtOAc, 0.0663 g, 0.404 mmol, 85%) as a white crystalline solid with a distinct eucalyptus/menthol/camphor scent. [α]$_D^{25}$+3.2 (c 0.13, CHCl$_3$); HPLC: Daicel Chiralpak AS-H, n-hex/1-PrOH=95/5, Flow Rate=1 mL/min, UV=230 nm, t$_R$=5.8 min and t$_R$=13.6 min (major, 71% ee).

Example 11

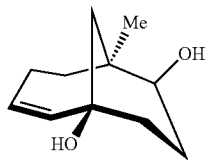

(1R,6S,7S)-6-methylbicyclo[4.3.1]dec-2-ene-1,7-diol (13)

To a solution of cyclononaepoxydiene 12 (R$_f$ 0.55 in 5:1 hex/EtOAc, 0.020 g, 0.122 mmol) in DCM (18 mL) at −78° C. was added BF$_3$.Et$_2$O (purified, redistilled, 0.0306 mL, 0.244 mmol) dropwise. After 15 min, the reaction was quenched by the addition of saturated aq. NaHCO$_3$ (1 mL). The resulting colorless solution was allowed to warm to room temperature. The mixture was extracted with DCM (3×15 mL). The combined organic layers were washed with brine (8 mL), dried over Na$_2$SO$_4$, filtered, and concentrated under reduced pressure to give a colorless oily residue. The crude product was purified by FCC (0 to 75% EtOAc/hex), affording the desired florlide core 13 (R$_f$ 0.15 in 1:1 EtOAc/hex, 0.0161 g, 0.089 mmol, 73%) as a white crystalline solid. [α]$_D^{25}$-3.6 (c 0.13, CHCl$_3$); IR ν$_{max}$ (thin film)/cm$^{-1}$ 3318, 3014, 2918, 2850, 1457, 1385, 1031, 1018. ESI-MS [M−H$_2$O+H]$^+$ m/z calcd 165.1, observed 165.00. ESI-MS [M+2Na]$^+$ m/z calcd 228.1, observed 228.5.

Example 12

Preparation of Compound 14

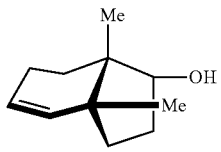

(3aR,7aS)-3a,7a-dimethyl-2,3,3a,6,7,7a-hexahydro-1H-inden-1-ol (14)

Zinc dust (0.025 g, 0.390 mmol) and bright red Cp$_2$TiCl$_2$ (0.050 g, 0.195 mmol) were weighed out under an inert atmosphere of dry argon. A solution of these metals in degassed THF (2.4 mL) with activated 4-angstrom powdered molecular sieves was stirred at room temperature in a flask covered in aluminum foil. After 25 minutes, the red solution had turned lime green, indicating complete reduction to Ti (III). To this was added a solution of the enantioenriched epoxyolefin 12 (0.008 g, 0.0488 mmol, azeotroped with excess toluene×3) in degassed THF (1.2 mL). The green color of the Ti(III) turned dark orange/light green. Complete consumption of the starting material was observed after 10 minutes. The crude product suspension was vacuum filtered into a small separatory funnel, rinsing through with liberal amounts of diethyl ether. The filtrate was partitioned between tetrahydrofuran/diethyl ether (3×10 mL) and brine (1 mL). The orange organic layer was washed with brine (1 mL), dried over sodium sulfate, filtered, and concentrated under reduced pressure. The orange residue was purified by FCC (0 to 20% diethyl ether/pentane), affording the xenibellol core compound 14 (R$_f$ 0.25 in 17% EtOAc/hex, 0.0037 g, 0.022 mmol, 46%) as a white crystalline solid with a distinct terpene scent. ESI-MS [M+Na]$^+$ m/z calcd 189.3, observed 188.5, 190.6.

Example 13

Preparation of Compound 4c and Compound 4d

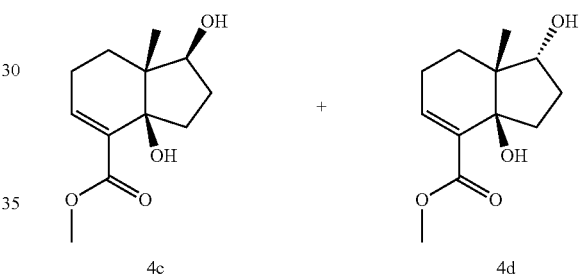

To a solution of TMS ether-alcohol 4 (3.29 g, 11.02 mmol) in THF (110 mL) at rt was added tetrabutylammonium fluoride (1M in THF, 14.32 mL, 14.32 mmol), producing an orange solution. After 3 hours, saturated aq NH$_4$Cl (20 mL) was added dropwise, and the quenched mixture was poured into water (80 mL). The organic layer was separated, and the aqueous layer was extracted with Et$_2$O (3×20 mL). The combined organic layers were washed with brine (15 mL), dried over Na$_2$SO$_4$, filtered, and concentrated under reduced pressure to a yellow oily residue. The crude material was purified by FCC (0 to 20% EtOAc/hexane, very slow increase in solvent gradient polarity), furnishing diol 4c (1.029 g, 41%) and diol 4d (1.396 g, 56%) as colorless oils. Complete separation is difficult to achieve, so a second column is usually required to maximize yields. Diol 4c: IR (neat) 3500, 2950, 2877, 2243, 1723, 1714, 1694, 1682, 1651, 1644, 1435, 1278, 1011 cm$^{-1}$; $^1$H NMR (500 MHz, CDCl$_3$) δ 6.90 (t, J=2.0 Hz, 1H), 4.18 (s, 1H), 3.75 (s, 3H), 3.68 (dd, J=11.0, 6.5 Hz, 1H), 3.05 (d, J=11.3 Hz, 1H), 2.42-2.29 (m, 2H), 2.28-2.12 (m, 2H), 1.99-1.84 (m, 2H), 1.47-1.29 (m, 2H), 1.08 (s, 3H) ppm; $^{13}$C NMR (125 MHz, CDCl$_3$) δ 167.7, 139.3, 133.4, 81.6, 81.4, 51.9, 48.3, 40.3, 32.1, 30.1, 23.5, 13.1 ppm; ESIMS m/z 249.9 (M+Na$^+$). Diol 4d: IR (neat) 3454, 2952, 2876, 1693, 1639, 1439, 1376, 1363, 1283, 1248, 1135, 1109, 1062, 1019 cm$^{-1}$; $^1$H NMR (400 MHz, CDCl$_3$) δ 6.99-6.91 (m, 1H), 4.37 (t, J=8.5 Hz, 1H), 3.84 (s, 1H), 3.74 (s, 3H), 2.35-2.17 (m, 3H), 2.12-1.96 (m, 2H), 1.72-1.55 (m, 3H), 1.51-1.38 (m, 1H), 1.03 (s, 3H) ppm; $^{13}$C NMR (75 MHz, CDCl$_3$) δ 167.8, 139.7, 134.0, 80.3, 79.8, 51.9, 46.6, 38.9, 29.4, 24.6, 23.0, 16.4 ppm; ESIMS m/z 249.8 (M+Na$^+$).

Diol 4d is readily recycled back to TMS ether 5 via the following sequence: To a solution of diol 4d (1.17 g, 5.19 mmol) in DCM (77 mL) at rt was added pyridinium dichromate (2.19 g, 5.71 mmol). The orange suspension turned dark brown within 1 h. After 8 h, Celite (2.595 g) was added to sequester the black tar byproduct. After 15 min, the suspension was vacuum filtered through Celite and rinsed through with liberal amounts of DCM. The filtrate was concentrated under reduced pressure to a dark brown oil (1.20 g, essentially pure ketol 3 by crude NMR). N-(Trimethylsilyl)imidazole (2.38 mL, 15.57 mmol) was added dropwise to crude ketol 3 at rt. After stirring the brown solution neat for 24 hours, it was cooled to 0° C. Saturated aq NH$_4$Cl (10 mL) was added dropwise, and the quenched mixture was extracted with DCM (3×10 mL). The combined organic layers were dried over Na$_2$SO$_4$, filtered, and concentrated under reduced pressure. Purification of the crude orange residue by FCC (0 to 17% EtOAc/hexane) furnished TMS ether 5 (0.800 g, 52% over 2 steps) as a colorless oil.

Example 14

Preparation of Compound 4 (wherein R$^d$=Ts=p-toluenesulfonyl)

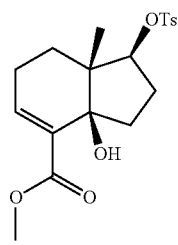

4

To a solution of diol 4c (1.09 g, 4.82 mmol) in pyridine (6.26 mL) at rt was added 1,4-diazabicyclo[2.2.2]octane (0.655 g, 5.78 mmol), 4-dimethylaminopyridine (0.059 g, 0.482 mmol), and p-toluenesulfonyl chloride (1.86 g, 9.63 mmol). After 14 h, the beige suspension had turned orange, and the mixture was cooled to 0° C. Brine (10 mL) was added dropwise, and the quenched mixture was extracted with DCM (3×15 mL). The combined organic layers were dried over Na$_2$SO$_4$, filtered, and concentrated under reduced pressure to a pale orange oil which slowly precipitated out colorless crystals upon standing. Purification of the crude material by FCC (0 to 33% EtOAc/hexane) furnished ester-tosylate 4c (1.674 g, 91%) as a colorless oil. IR (neat) 3521, 2951, 2928, 1693, 1438, 1357, 1282, 1247, 1188, 1175, 1100, 971, 667, 556 cm$^{-1}$; $^1$H NMR (500 MHz, CDCl$_3$) δ 7.79 (d, J=8.2 Hz, 2H), 7.32 (d, J=8.5 Hz, 2H), 6.90 (t, J=3.9 Hz, 1H), 4.53 (t, J=6.8 Hz, 1H), 3.74 (s, 3H), 3.73 (s, 1H), 2.44 (s, 3H), 2.32-2.04 (m, 3H), 2.02-1.93 (m, 2H), 1.87-1.76 (m, 1H), 1.51-1.36 (m, 2H), 1.02 (s, 3H) ppm; $^{13}$C NMR (125 MHz, CDCl$_3$) δ 167.8, 144.6, 139.7, 134.5, 133.9, 129.9, 127.9, 86.8, 78.1, 52.0, 47.6, 37.8, 29.9, 28.7, 22.9, 21.8, 14.6 ppm; ESIMS m/z 403.1 (M+Na$^+$).

Example 15

Preparation of Compound 20

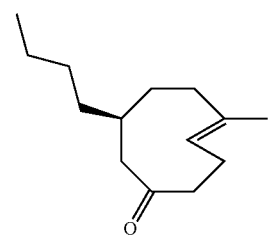

20

To a degassed solution of cyclononadienone-carboxylic acid 2 (0.029 g, 0.149 mmol, azeotropically dried with toluene×3) in THF (1 mL, trace HMPA present) at −40° C. was added n-BuLi (2.5M in hexanes, 0.19 mL, 0.475 mmol) and TMSCl (redistilled, 0.030 mL, 0.243 mmol). After 2 h, the pale yellow solution was warmed to rt and more TMSCl (redistilled, 0.059 mL, 0.464 mmol) was added. After 30 min, the solution was cooled to −78° C. Bu$_2$Cu(CN)Li$_2$ was simultaneously prepared by adding n-BuLi (2.5M in hexanes, 0.41 mL, 1.03 mmol) to a degassed suspension of activated CuCN (0.0457 g, 0.510 mmol) in THF (5.1 mL) at −78° C., generating a pale yellow solution within 5 min. After stirring the cuprate for 1 h, the solution of in situ silyl ester was added dropwise via cannula to the cuprate solution at −78° C. After 3 h, saturated aq 20% NH$_4$OH/NH$_4$Cl (5 mL) was added dropwise, and the mixture was vigorously stirred while warming to rt. The blue aqueous layer was extracted with Et$_2$O (3×5 mL). The combined organic layers were washed with brine (3 mL), dried over Na$_2$SO$_4$, filtered, and concentrated under reduced pressure to an oily yellow residue. Purification of the crude material by FCC (0 to 17% EtOAc/hexane) furnished compound 20 (0.009 g, 29%) as a colorless oil. Decarboxylation of the crude product was presumably acid-catalyzed. IR (neat) 2956, 2926, 2870, 2856, 1810, 1702, 1456, 1384, 1169, 1101 cm$^{-1}$; 7.87:1 conformational equilibrium (25° C.); $^1$H NMR, major conformer (500 MHz, CDCl$_3$) δ 5.34 (dd, J=10.5, 5.5 Hz, 1H), 2.66-2.56 (m, 1H), 2.53-2.46 (m, 1H), 2.45-2.38 (m, 1H), 2.16-2.05 (m, 4H), 1.92 (td, J=12.5, 4.0 Hz, 1H), 1.79 (br s, 1H), 1.64 (d, J=1.5 Hz, 3H), 1.59-1.54 (m, 1H), 1.31 (br s, 7H), 0.89 (br s, 3H) ppm; $^{13}$C NMR, major conformer (125 MHz, CDCl$_3$) δ 215.0, 137.5, 123.6, 54.5, 41.0, 40.5, 39.5, 37.2, 35.2, 29.3, 23.2, 23.0, 16.9, 14.3 ppm; ESIMS m/z 209.1 (M+H$^+$), 226.0 (M+H$_2$O$^+$).

Example 16

Preparation of Compound 10

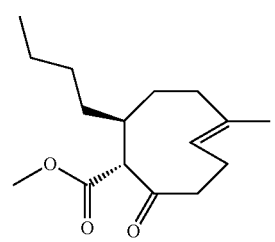

10

To a degassed suspension of activated CuCN (0.0434 g, 0.480 mmol) in THF (4.8 mL) at −78° C. was added n-BuLi (2.5M in hexanes, 0.384 mL, 0.960 mmol), generating a pale yellow/light brown solution within 5 min. After 15 min at −78° C., TMSCl (redistilled, 0.062 mL, 0.480 mmol) was added followed immediately by a degassed solution of cyclononadienone-carboxylate-methyl ester 1 (0.017 g, 0.082 mmol, azeotropically dried with toluene×3) in THF (1 mL), producing a dark yellow solution. After 5 min, saturated aq 20% NH$_4$OH/NH$_4$Cl (3 mL) was added dropwise, and the mixture was vigorously stirred while warming to rt. The blue aqueous layer was extracted with Et$_2$O (3×5 mL). The combined organic layers were washed with brine (2 mL), dried over Na$_2$SO$_4$, filtered, and concentrated under reduced pressure to an oily yellow residue. Purification of the crude material by FCC (0 to 5% EtOAc/hexane) furnished 10 (0.013 g, 60%) as a colorless oil. Extensive 2D NMR analysis and comparisons with computational modeling[2] confirmed the trans stereochemistry in both conformations. Variable temperature $^1$H NMR (up to 90° C. in tol-d$_8$) did not show a significant shift in conformational equilibrium. IR (neat) 2952, 2932, 2859, 1737, 1705, 1454, 1434, 1193, 1148 cm$^{-1}$; 4.51:1 conformational equilibrium (25° C.); $^1$H NMR, major conformer (400 MHz, CDCl$_3$) δ 5.41 (dd, J=11.6, 3.2 Hz, 1H), 3.67 (s, 3H), 3.12 (d, J=10.0 Hz, 1H), 3.02-2.92 (m, 1H), 2.75-2.61 (m, 1H), 2.24-2.12 (m, 2H), 2.11-1.97 (m, 2H), 1.90 (td, J=12.0, 3.2 Hz, 1H), 1.56 (s, 3H), 1.45-1.15 (m, 8H), 0.95-0.83 (m, 3H) ppm; $^{13}$C NMR, major conformer (100 MHz, CDCl$_3$) δ 207.5, 170.8, 137.0, 123.8, 70.1, 52.1, 40.1, 39.6, 38.9, 35.0, 31.7, 28.8, 24.6, 23.0, 17.6, 14.2 ppm; ESIMS m/z 266.9 (M+H$^+$), 283.9 (M+H$_2$O$^+$).

Example 17

Preparation of Compounds 23 and 24

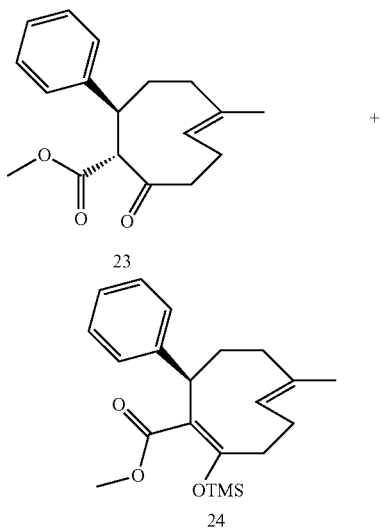

To a degassed suspension of activated CuCN (0.0543 g, 0.600 mmol) in Et$_2$O (6.0 mL) at −78° C. was added PhLi (1.8M in n-Bu$_2$O, 0.667 mL, 1.200 mmol), generating a dark yellow color within 5 min. The cuprate was warmed to 0° C., turning into a bright yellow solution. After cooling back to −78° C. and stirring for 15 min, TMSCl (redistilled, 0.077 mL, 0.600 mmol) was added followed immediately by a degassed solution of cyclononadienone-carboxylate-methyl ester 1 (0.020 g, 0.096 mmol, azeotropically dried with toluene×3) in Et$_2$O (1 mL), producing a dark olive green/light brown solution. After 15 min, saturated aq 20% NH$_4$OH/NH$_4$Cl (3 mL) was added dropwise, and the mixture was vigorously stirred while warming to rt. The blue aqueous layer was extracted with Et$_2$O (3×6 mL). The combined organic layers were washed with brine (3 mL), dried over Na$_2$SO$_4$, filtered, and concentrated under reduced pressure to a pale yellow oil in n-Bu$_2$O. Purification of the crude material by FCC (0 to 10% Et$_2$O/pentane) furnished 23 (0.012 g, 44%) and 24 (0.010 g, 29%) as colorless oils. The relative stereochemistry of 23 was assigned by analogy. TMS-enol ethers are known to be stable to these workup conditions. Compound 24 is slowly hydrolyzed back to compound 23 on TLC and silica gel. Compound 23: IR (neat) 3084, 3060, 3028, 2933, 2856, 1737, 1703, 1452, 1434, 1201, 1163, 1147, 701 cm$^{-1}$; 6.12:1 conformational equilibrium (25° C.); $^1$H NMR, major conformer (400 MHz, CDCl$_3$) δ 7.29-7.23 (m, 3H), 7.21-7.15 (br d, J=7.2 Hz, 2H), 5.61 (dd, J=11.6, 4.0 Hz, 1H), 3.61 (d, J=10.4 Hz, 1H), 3.47-3.38 (m, 1H), 3.26 (s, 3H), 3.20-3.08 (m, 1H), 2.76 (ddd, J=16.8, 11.2, 5.6 Hz, 1H), 2.26-2.18 (m, 1H), 2.17-2.10 (m, 1H), 2.09-2.02 (m, 2H), 1.94-1.81 (m, 2H), 1.62 (s, 3H) ppm; $^{13}$C NMR, major conformer (100 MHz, CDCl$_3$) δ 207.0, 169.4, 145.5, 136.6, 128.5, 127.9, 126.6, 124.5, 71.6, 51.9, 46.5, 40.1, 38.8, 35.2, 24.8, 17.4 ppm; ESIMS m/z 255.1 (M-MeOH+H$^+$), 287.0 (M+H$^+$), 304.0 (M+H$_2$O$^+$). Compound 24: IR (neat) 3085, 3057, 3023, 2949, 2936, 2864, 2848, 1698, 1598, 1444, 1433, 1280.2, 1252, 1236, 1213, 1156, 1139, 1100, 1076, 1054, 890, 859, 846 cm$^{-1}$; $^1$H NMR (300 MHz, CDCl$_3$) δ 7.34-7.27 (m, 4H), 7.22-7.14 (m, 1H), 4.88 (d, J=10.5 Hz, 1H), 4.42 (dd, J=10.5, 6.3 Hz, 1H), 3.82 (d, J=0.6 Hz, 3H), 3.67-3.52 (m, 1H), 2.51-2.26 (m, 4H), 2.25-2.01 (m, 3H), 1.74 (s, 3H), −0.03 (d, J=0.9 Hz, 9H) ppm; $^{13}$C NMR (75 MHz, CDCl$_3$) δ 171.9, 166.8, 146.0, 137.9, 128.0, 126.9, 125.6, 125.3, 120.5, 51.7, 43.8, 39.3, 32.3, 28.2, 22.7, 17.1, 0.7 ppm; ESIMS m/z 287.1 (M-TMS+H$^+$), 327.1 (M-MeOH+H$^+$), 358.9 (M+H$^+$).

Example 18

Preparation of Compound 25

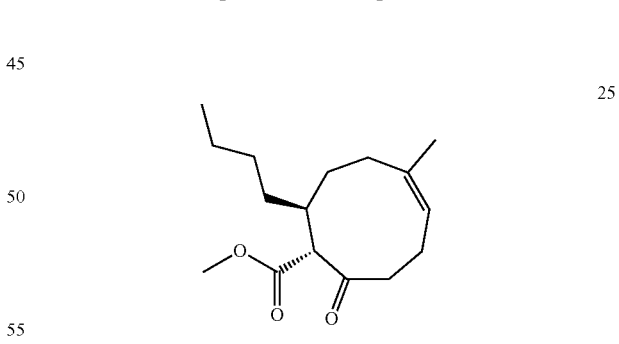

A 10 mL microwave reaction tube was charged with compound 22 (4.51:1 conformational equilibrium (CDCl$_3$, 25° C.), 0.001 g, 0.00375 mmol), DMSO-d$_6$ (0.75 mL), and a Teflon stir bar. The reaction tube was sealed with a Teflon-lined snap cap, and heated in a microwave reactor at 150° C. (250 W, 25-50 psi) for 30 minutes under efficient stirring (setting="HIGH"). After cooling with compressed air flow, the crude pale yellow solution was poured into brine (7.5 mL) and extracted with Et$_2$O (3×1.5 mL). The combined organic layers were washed with brine (0.25 mL), dried over Na$_2$SO$_4$, filtered, and concentrated under reduced pressure, furnishing 25 (0.001 g, quant crude yield) as a colorless solid. 2.37:1 conformational equilibrium (CDCl$_3$, 25° C.); $^1$H NMR, major conformer (500 MHz, CDCl$_3$) δ 5.52 (t, J=4.5 Hz, 1H), 3.68 (d, J=2.0 Hz, 3H), 3.35 (d, J=11.3 Hz, 1H), 2.89 (t, J=11.3 Hz, 1H), 2.54-2.44 (m, 1H), 2.35 (td, J=7.8, 2.0 Hz, 1H), 2.25-2.09 (m, 4H), 1.76-1.67 (m, 2H), 1.64 (s, 3H), 1.36-1.17 (br s, 6H), 0.88 (t, J=5.8 Hz, 3H) ppm; $^{13}$C NMR, major conformer (125 MHz, CDCl$_3$) δ 210.7, 170.0, 138.3, 124.7, 66.0, 52.4, 40.2, 34.9, 33.8, 30.5, 28.9, 24.7, 22.9, 22.4, 15.4, 14.1 ppm.

Examples 19 and 20

General Procedure for Tebbe Olefination of β-Keto Esters to Exo-Olefin Esters in Examples 19 and 20

To a degassed solution of β-keto ester (1 eq, azeotropically dried with toluene×3) in THF/pyridine (5:1, 0.02 M) at 0° C. was added Tebbe reagent (0.5M in toluene, 1 eq). The deep orange solution was warmed to rt. If the reaction was incomplete, the solution was cooled back to 0° C. and more Tebbe reagent (0.5M in toluene, 1 eq) was added. This cooling-adding-warming process was repeated until starting material was completely consumed, generally within 1 h. The brown solution was diluted with Et$_2$O to a volume of ~5 mL and cooled to 0° C. MeOH (1 mL) was added dropwise, generating a creamy orange/red suspension. The quenched mixture was vacuum filtered through Celite and rinsed through with liberal amounts of Et$_2$O. The orange filtrate was washed with brine (10 mL). The organic layer was dried over Na$_2$SO$_4$, filtered, and concentrated under reduced pressure to an oily orange residue. Pure exo-olefin ester was secured by FCC (Et$_2$O/pentane gradual solvent gradient).

Example 19

Preparation of Compound 26

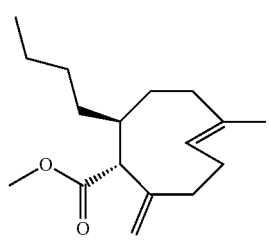

26

Following the general Tebbe olefination procedure, compound 26 was obtained as a colorless amorphous solid in 85% yield (0.0037 g). IR (thin film) 2954, 2922, 2852, 1737, 1659, 1631, 1552, 1451, 1384, 1148 cm$^{-1}$; 5.38:1 conformational equilibrium (25° C.); $^1$H NMR, major conformer (500 MHz, C$_6$D$_6$) δ 5.38 (dd, J=11.7, 3.3 Hz, 1H), 4.98 (s, 1H), 4.84 (s, 1H), 3.32 (s, 3H), 2.89 (d, J=10.5 Hz, 1H), 2.48 (tdd, J=7.0, 5.3, 1.8 Hz, 1H), 2.32-2.21 (m, 2H), 2.19 (br d, J=12.5 Hz, 1H), 2.15-2.08 (m, 1H), 1.99-1.92 (m, 2H), 1.53 (s, 3H), 1.49-1.15 (m, 8H), 0.95-0.86 (m, 3H) ppm; $^{13}$C NMR, major conformer (125 MHz, C$_6$D$_6$) δ 173.8, 146.3, 135.5, 124.9, 118.6, 63.4, 53.3, 51.0, 39.2, 35.7, 32.5, 32.0, 29.7, 29.3, 23.4, 18.6, 14.3 ppm; ESIMS m/z 265.1 (M+H$^+$).

Example 19

Preparation of Compound 27

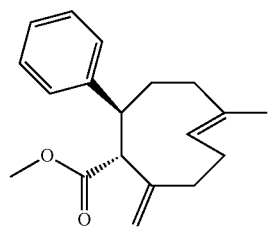

27

Following the general Tebbe olefination procedure, compound 27 was obtained as a colorless oil in 86% yield (0.0102 g). IR (neat) 3062, 3027, 2975, 2928, 2857, 1734, 1449, 1433, 1324, 1199, 1163, 1145, 892, 757, 701 cm$^{-1}$; 6.28:1 conformational equilibrium (25° C.); $^1$H NMR, major conformer (300 MHz, C$_6$D$_6$) δ 7.21-7.10 (m, 4H), 7.08-6.98 (m, 1H), 5.47 (dd, J=12.0, 3.6 Hz, 1H), 5.03 (s, 1H), 4.84 (s, 1H), 3.37 (d, J=11.4 Hz, 1H), 3.29-3.19 (m, 1H), 2.94 (s, 3H), 2.62-2.49 (m, 1H), 2.28 (td, J=12.0, 4.8 Hz, 1H), 2.17 (br d, J=14.4 Hz, 1H), 1.95 (td, J=12.3, 3.0 Hz, 1H), 1.85-1.76 (m, 1H), 1.72-1.61 (m, 1H), 1.49 (s, 3H), 1.56 (dd, J=5.3, 2.5 Hz, 1H), 1.09 (t, J=7.1 Hz, 1H) ppm; $^{13}$C NMR, major conformer (125 MHz, CDCl$_3$) δ 172.9, 147.4, 145.2, 135.6, 128.4, 128.0, 126.1, 124.9, 119.8, 64.9, 51.3, 45.9, 40.0, 36.0, 31.5, 29.0, 18.6 ppm; ESIMS m/z 253.0 (M–MeOH+H$^+$), 285.0 (M+H$^+$).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula 1:

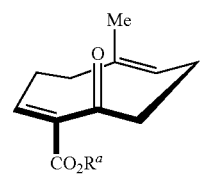

1 wherein:
R$^a$ is H, (C$_1$-C$_6$)alkyl, (C$_2$-C$_6$)alkenyl, (C$_2$-C$_6$)alkynyl, (C$_3$-C$_8$)cycloalkyl, (C$_3$-C$_8$)cycloalkyl(C$_1$-C$_6$)alkyl, aryl, or heteroaryl, wherein each (C$_1$-C$_6$)alkyl, (C$_2$-C$_6$)alkenyl, (C$_2$-C$_6$)alkynyl, (C$_3$-C$_8$)cycloalkyl, and (C$_3$-C$_8$)cycloalkyl(C$_1$-C$_6$)alkyl of R$^a$ is optionally substituted with one or more groups independently selected from halo, hydroxy, cyano, nitro, (C$_1$-C$_6$)alkoxy, (C$_3$-C$_8$)cycloalkyl, oxo, carboxy, aryl, aryloxy, and —NR$^b$R$^c$; and wherein each aryl, and heteroaryl of R$^a$ is optionally substituted with one or more groups independently selected from (C$_1$-C$_6$)

alkyl, halo, hydroxy, cyano, carboxy, nitro, trifluoromethyl, trifluoromethoxy, $(C_1$-$C_6)$alkoxy, $(C_1$-$C_6)$alkoxycarbonyl, $(C_1$-$C_6)$alkanoyloxy, and —$NR^bR^c$; and $R^b$ and $R^c$ are each independently selected from H, $(C_1$-$C_6)$alkyl, $(C_3$-$C_8)$cycloalkyl, $(C_3$-$C_8)$cycloalkyl($C_1$-$C_6)$alkyl, aryl, heteroaryl, aryl($C_1$-$C_6$) alkyl and heteroaryl($C_1$-$C_6)$alkyl; or $R^b$ and $R^c$ together with the nitrogen to which they are attached form a aziridino, azetidino, morpholino, piperazino, pyrrolidino or piperidino.

2. A method for preparing an ester of formula 1:

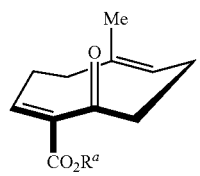

1 wherein $R^a$ is methyl;

comprising treating an acid of formula 2:

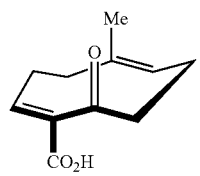

2 with $(Me)_2SiCHN_2$ in methanol at about 0° C. to provide the ester of formula 1.

3. A compound of formula 2, 10, 11b, 12, 13, 20, 23, 24, 25, 26, or 27:

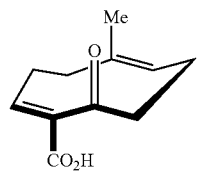

2

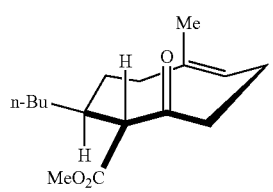

10

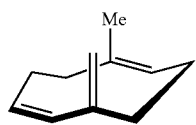

11b

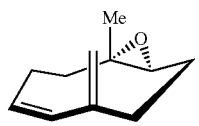

12

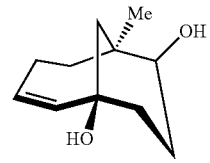

13

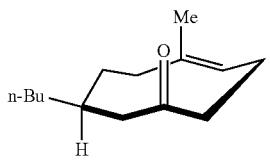

20

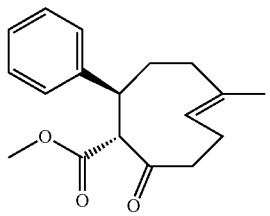

23

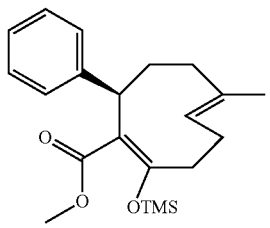

24

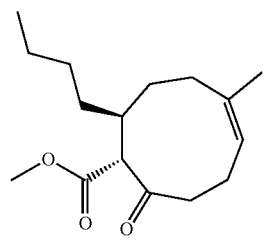

25

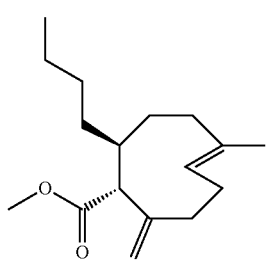

26

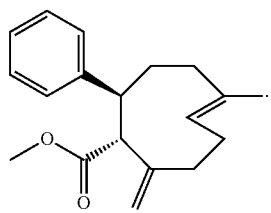

UNITED STATES PATENT AND TRADEMARK OFFICE
CERTIFICATE OF CORRECTION

PATENT NO. : 8,809,558 B1
APPLICATION NO. : 13/215931
DATED : August 19, 2014
INVENTOR(S) : Williams et al.

It is certified that error appears in the above-identified patent and that said Letters Patent is hereby corrected as shown below:

In the Specification

In Column 1, Lines 5-9 under the Statement of Government Rights:

Replace

The invention was made with the support of a grant from the National Science Foundation (Grant No: CHE-1012379). The Government has certain rights in the invention.

With the following revised paragraph:

This invention was made with government support under CHE-1012379 awarded by the National Science Foundation. The government has certain rights in the invention.

In the Claims

In Claim 2, Column 35, Line 39:

Replace $(Me)_2SiCHN_2$ with $(Me)_3SiCHN_2$

Signed and Sealed this
Eighth Day of September, 2015

Michelle K. Lee
*Director of the United States Patent and Trademark Office*